(12) United States Patent
Yiannikouros et al.

(10) Patent No.: US 9,388,154 B2
(45) Date of Patent: Jul. 12, 2016

(54) PROCESS FOR PREPARING SYNTHETIC PROSTACYCLINS

(75) Inventors: George Petros Yiannikouros, Florence, SC (US); Panos Kalaritis, Florence, SC (US); Chaminda Priyapushpa Gamage, Florence, SC (US); Denis Viktorovich Arefyev, Florence, SC (US)

(73) Assignee: Lund Biotechnology PBC, Silver Spring, MD (US)

( * ) Notice: Subject to any disclaimer, the term of this patent is extended or adjusted under 35 U.S.C. 154(b) by 0 days.

(21) Appl. No.: 14/343,550

(22) PCT Filed: Sep. 12, 2012

(86) PCT No.: PCT/US2012/054910
§ 371 (c)(1),
(2), (4) Date: Aug. 14, 2014

(87) PCT Pub. No.: WO2013/040068
PCT Pub. Date: Mar. 21, 2013

(65) Prior Publication Data
US 2015/0025255 A1    Jan. 22, 2015

Related U.S. Application Data

(60) Provisional application No. 61/533,622, filed on Sep. 12, 2011.

(51) Int. Cl.
| | | |
|---|---|---|
| C07C 67/31 | (2006.01) | |
| C07C 69/738 | (2006.01) | |
| C07C 405/00 | (2006.01) | |
| C07C 67/313 | (2006.01) | |
| C07D 307/93 | (2006.01) | |
| A61K 31/5585 | (2006.01) | |
| A61K 31/557 | (2006.01) | |
| A61K 31/5575 | (2006.01) | |
| A61K 31/5578 | (2006.01) | |

(52) U.S. Cl.
CPC ............ *C07D 307/93* (2013.01); *A61K 31/557* (2013.01); *A61K 31/5575* (2013.01); *A61K 31/5578* (2013.01); *A61K 31/5585* (2013.01); *C07C 67/31* (2013.01); *C07C 67/313* (2013.01); *C07C 405/00* (2013.01); *C07C 2101/10* (2013.01)

(58) Field of Classification Search
CPC .... C07D 307/93; C07D 67/31; C07D 69/738; C07D 2101/10; C07D 405/00; C07D 67/313; A61K 31/5585
USPC .................................................. 549/458, 214
See application file for complete search history.

(56) References Cited

U.S. PATENT DOCUMENTS

| | | | | |
|---|---|---|---|---|
| 4,311,644 | A * | 1/1982 | Moniot et al. ................ | 549/465 |
| 4,810,805 | A * | 3/1989 | Shibasaki et al. ............. | 549/421 |
| 4,880,939 | A * | 11/1989 | Ohno et al. .................... | 549/458 |
| 5,700,833 | A * | 12/1997 | Watanabe et al. ............. | 514/510 |
| 7,005,527 | B2 * | 2/2006 | Szabo et al. ................... | 549/214 |
| 2002/0087025 | A1 | 7/2002 | Moriarty et al. | |

FOREIGN PATENT DOCUMENTS

| | | |
|---|---|---|
| JP | 6-62600 B2 | 8/1994 |
| WO | WO 03/011849 A1 | 2/2003 |

OTHER PUBLICATIONS

Wakita et al Tetrahedron 55 (1999) 2449-2474.*
Berge et al., "Review Article, Pharmaceutical Salts," Journal of Pharmaceutical Sciences, Jan. 1977, 66(1)1-19.

\* cited by examiner

*Primary Examiner* — Erich A Leeser
(74) *Attorney, Agent, or Firm* — Foley & Lardner LLP

(57) ABSTRACT

The presently disclosed subject matter provides methods of preparing synthetic prostacyclin analogs, including Beraprost, either as racemic mixtures or as single stereoisomers. Also provided are novel synthetic intermediates for use in these methods.

19 Claims, No Drawings

PROCESS FOR PREPARING SYNTHETIC PROSTACYCLINS

CROSS REFERENCE TO RELATED APPLICATIONS

This application is the U.S. National Stage of PCT/US2012/054910, filed Sep. 12, 2012, which claims the benefit of U.S. Provisional Patent Application Ser. No. 61/533,622, filed Sep. 12, 2011, the disclosure of which is incorporated herein by reference in its entirety.

TECHNICAL FIELD

The presently disclosed subject matter relates to the synthesis of prostacyclins, prostacyclin analogues, and/or synthetic intermediates thereof, and in some embodiments to the synthesis of single stereoisomers of the prostacyclins, analogues and/or intermediates, instead of stereoisomer mixtures. The presently disclosed subject matter further relates to novel compounds that can be used in the synthesis of the prostacyclins, prostacyclin analogues and/or synthetic intermediates.

BACKGROUND

Beraprost (i.e., 2,3,3a,8b-tetrahydro-2-hydroxy-1-(3-hydroxy-4-methyl-1-octen-6-ynyl)-1H-cyclopenta(b)benozofuran-5-butanoic acid) is a synthetic prostacyclin analogue that can inhibit platelet aggregation and can affect vasodilation, which in turn can lower blood pressure. Beraprost is orally available and is used, for example, in the treatment of pulmonary hypertension, chronic peripheral vascular disease, and arterial thrombosis.

Current synthetic processes for producing Beraprost can be lengthy and expensive. Additionally, the currently marketed form of Beraprost is a mixture of four isomers even though only one of the isomers is pharmacologically active.

Accordingly, there remains a need in the art for additional methods of synthesizing Beraprost and other synthetic prostacyclin analogues, such as but not limited to, more versatile and efficient methods, and methods that can provide single isomer compounds.

SUMMARY

In some embodiments, the presently disclosed subject matter provides a method for preparing a synthetic prostacyclin or a synthetic intermediate thereof, wherein the method comprises contacting an aldehyde with an enantiomerically pure phosphonate in a Horner-Emmons reaction to provide an alkene. In some embodiments, the synthetic prostacyclin or synthetic intermediate thereof is provided as a single isomer.

In some embodiments, the aldehyde is a product of the ozonolysis of a compound of formula (V), (V') or (V"):

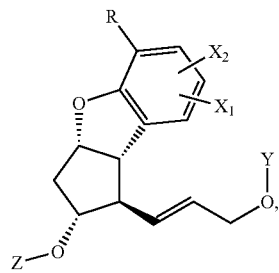

(V)

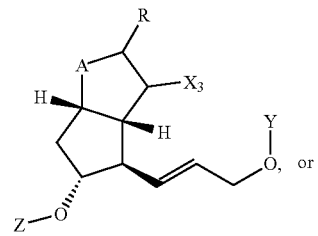

(V')

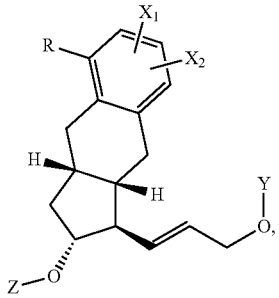

(V")

wherein R is a directly attached carboxylic acid or ester group or is a carboxylic acid or ester group attached via an aliphatic linker, optionally wherein the aliphatic linker is branched or substituted; $X_1$ and $X_2$ are independently H or an aryl group substituent; $X_3$ is H or an alkyl group substituent; A is —O—, —S—, or —$CH_2$—; and Y and Z are hydroxyl protecting groups, which can be the same or different; or a stereoisomer thereof.

In some embodiments, R is —$CO_2R'$, —$(CH_2)_n$—$CO_2R'$, —O—$(CH_2)_n$—$CO_2R'$, or —$CH_2$=$CH_2$—$(CH_2)_n$—$CO_2R'$, wherein n is an integer between 1 and 8 and R' is H, unsubstituted alkyl, substituted alkyl, aryl, or substituted aryl. In some embodiments, Y and Z are each —C(=O)$CH_3$. In some embodiments, the aldehyde is the product of the ozonolysis of a compound of formula (V) wherein R is a directly attached carboxylic acid or ester group or is a carboxylic acid or ester group attached via an aliphatic linker, optionally wherein the aliphatic linker is branched or substituted; $X_1$ and $X_2$ are independently H or an aryl group substituent; and Y and Z are hydroxyl protecting groups, which can be the same or different; or a stereoisomer thereof. In some embodiments, the compound of formula (V) is the compound:

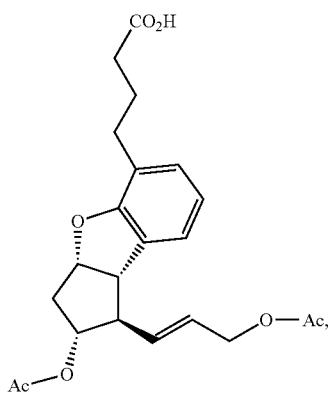 [SMILES: CC(=O)OC/C=C/[C@@H]1[C@H]2c3cccc(CCCC(=O)O)c3O[C@H]2C[C@H]1OC(C)=O]

or a stereoisomer thereof.

In some embodiments, the enantiomerically pure phosphonate has a structure:

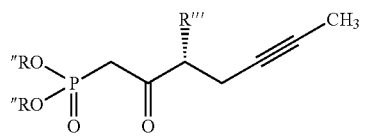

or

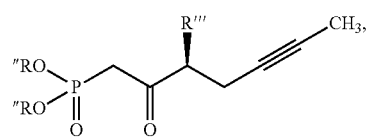

wherein R" and R''' are alkyl.

In some embodiments, the method further comprises stereoselectively reducing a ketone in the alkene compound formed during the Horner-Emmons reaction. In some embodiments, the stereoselective reduction is performed using a Corey-Bakshi-Shibata (CBS) catalyst. In some embodiments, the method further comprises deprotecting protected hydroxyl groups. In some embodiments, the synthetic prostacyclin is Beraprost.

In some embodiments, the presently disclosed subject matter provides a synthetic prostacyclin or synthetic intermediate thereof, prepared according to a method comprising contacting an aldehyde with an enantiomerically pure phosphonate in a Horner-Emmons reaction to provide an alkene. In some embodiments, the synthetic prostacyclin is a single isomer of Beraprost.

In some embodiments, the presently disclosed subject matter provides a method for preparing a synthetic prostacyclin or synthetic intermediate thereof, wherein the method comprises: (a) providing a compound of formula (V), (V') or (V"); (b) deprotecting the compound of formula (V), (V') or (V") to provide a diol comprising a primary alcohol and a secondary alcohol; and (c) selectively oxidizing the primary alcohol of the diol to provide an aldehyde-containing compound of one of formulas (XIII), (XIII') or (XIII"):

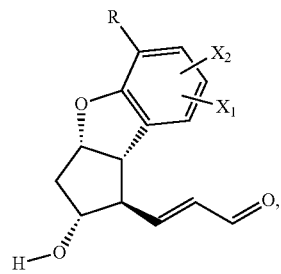

(XIII)

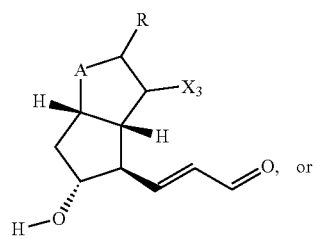

(XIII')

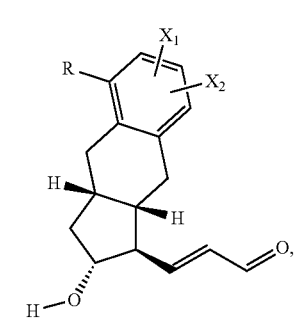

(XIII")

or a stereoisomer thereof, wherein R, $X_1$, $X_2$, $X_3$, and A are as defined for the compounds of formulas (V), (V'), and (V").

In some embodiments, the method further comprises: (d) protecting the aldehyde-containing compound to provide a protected compound; (e) alkylating the protected compound with a chiral alkyne-containing compound to provide an alkylated compound; and (f) deprotecting the alkylated compound to provide a ketone-containing compound. In some embodiments, the ketone-containing compound has a structure of one of formulas (Xb), (Xb'), and (Xb"):

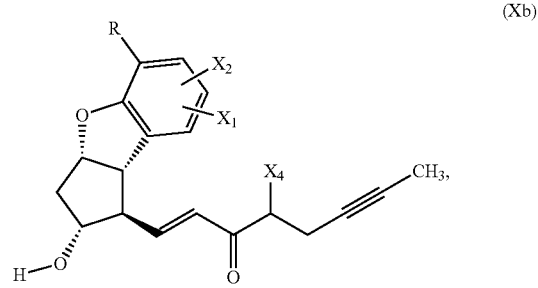

(Xb)

-continued

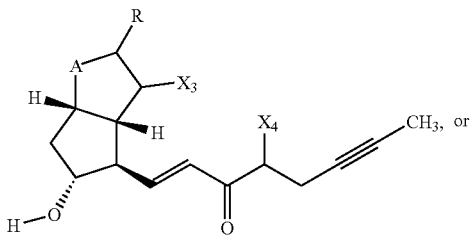

(Xb')

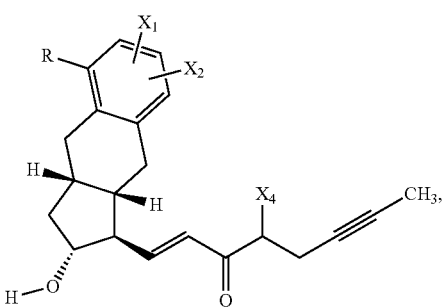

(Xb")

wherein R is a directly attached carboxylic acid or ester group or is a carboxylic acid or ester group attached via an aliphatic linker, optionally wherein the aliphatic linker is branched or substituted; $X_1$ and $X_2$ are independently H or an aryl group substituent; $X_3$ is H or an alkyl group substituent; A is —O—, —S—, or —CH$_2$—; and $X_4$ is H, $$\overset{X_5}{\overline{\vdots}} \text{ or } \overset{X_5}{\downarrow},$$

wherein $X_5$ is alkyl;
or a stereoisomer thereof.

In some embodiments, the method further comprises stereoselectively reducing the ketone of the ketone-containing compound to provide a synthetic prostacyclin. In some embodiments, the stereoselective reduction is performed using a Corey-Bakshi-Shibata (CBS) catalyst. In some embodiments, the synthetic prostacyclin is Beraprost, Iloprost, or Icaprost.

In some embodiments, the method further comprises the reduction of alkyne or both alkyne and alkene bonds. In some embodiments, the synthetic prostacyclin is Prostacyclin, Carbaprostacyclin, or Treprostinil.

In some embodiments, the synthetic prostacyclin or synthetic intermediate thereof is provided as a single isomer.

In some embodiments, the presently disclosed subject matter provides a synthetic prostacyclin or synthetic intermediate thereof, prepared according to a method comprising: (a) providing a compound of formula (V), (V') or (V''); (b) deprotecting the compound of formula (V), (V') or (V'') to provide a diol comprising a primary alcohol and a secondary alcohol; and (c) selectively oxidizing the primary alcohol of the diol to provide an aldehyde-containing compound of one of formulas (XIII), (XIII') or (XIII''). In some embodiments, the synthetic prostacyclin is a single isomer of Beraprost, Iloprost, Icaprost, Prostacyclin, Carbaprostacyclin, or Treprostinil.

In some embodiments, the presently disclosed subject matter provides a method for producing a compound of formula (V), wherein the method comprises: (a) coupling compound A:

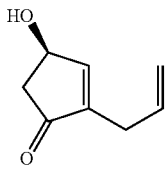

(A)

or a stereoisomer thereof, and a compound of formula (B):

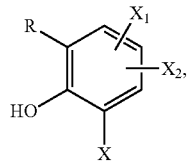

(B)

wherein X is halo; R is a directly attached carboxylic acid or ester group or is a carboxylic acid or ester group attached via an aliphatic linker, optionally wherein the aliphatic linker is branched or substituted; and $X_1$ and $X_2$ are independently H or an aryl group substituent; (b) cyclizing the product of step (a) to form a cyclized compound; (c) reducing a ketone group in the cyclized compound to a form a compound comprising a secondary alcohol; and (d) performing an oxidative rearrangement of the compound prepared in step (c) or a compound prepared by protecting the secondary alcohol group of the compound prepared in step (c).

In some embodiments, the coupling of step (a) is a Mitsunobu-type coupling. In some embodiments, the cyclizing of step (b) is a radical-type cyclization. In some embodiments, the oxidative rearrangement is performed in the presence of a palladium (II) catalyst.

In some embodiments, the presently disclosed subject matter provides a compound prepared according to the method comprising: (a) coupling compound A or a stereoisomer thereof, and a compound of formula (B); (b) cyclizing the product of step (a) to form a cyclized compound; (c) reducing a ketone group in the cyclized compound to a form a compound comprising a secondary alcohol; and (d) performing an oxidative rearrangement of the compound prepared in step (c) or a compound prepared by protecting the secondary alcohol group of the compound prepared in step (c).

In some embodiments, the presently disclosed subject matter provides a method for preparing a synthetic prostacyclin or synthetic intermediate thereof, wherein the method comprises the use of a synthetic intermediate of formula (V), (V'), or (V'') or a stereoisomer thereof, or a hydroxyl group deprotected derivative thereof, wherein the hydroxyl group deprotected derivative thereof is a compound of one of formulas (V), (V'), and (V'') wherein one or both of Z and Y are replaced by a hydrogen atom.

In some embodiments, R is —CO$_2$R', —(CH$_2$)$_n$—CO$_2$R', —O—(CH$_2$), —CO$_2$R', or —CH$_2$=CH$_2$—(CH$_2$)$_n$—CO$_2$R, wherein n is an integer between 1 and 8, and R' is H, unsubstituted alkyl, substituted alkyl, aryl, or substituted aryl. In some embodiments, R is —(CH$_2$)$_n$—CO$_2$R'. In some embodiments, R' is H or unsubstituted alkyl. In some embodiments, n is 3 and R' is H or methyl.

In some embodiments, $X_1$ and $X_2$ are independently selected from the group consisting of H, alkyl, substituted alkyl, aryl, substituted aryl, alkoxy, aryloxy, alkylthio, arylthio, —OH, —SH. In some embodiments, $X_1$ and $X_2$ are each H.

In some embodiments, one or both of Y and Z are present and are —C(=O)R'''', wherein R'''' is alkyl, substituted alkyl, aralkyl, aryl, or substituted aryl. In some embodiments, Y and Z are both present and are —C(=O)CH$_3$.

In some embodiments, the synthetic prostacyclin or synthetic intermediate thereof is a single isomer.

In some embodiments, the presently disclosed subject matter provides a synthetic prostacyclin or synthetic intermediate thereof prepared according to a method comprising the use of a synthetic intermediate of formula (V), (V'), or (V") or a stereoisomer thereof, or a hydroxyl group deprotected derivative thereof.

In some embodiments, the presently disclosed subject matter provides a compound of formula (V), (V'), or (V") or a hydroxyl group deprotected derivative thereof, wherein formulas (V), (V'), and (V") are:

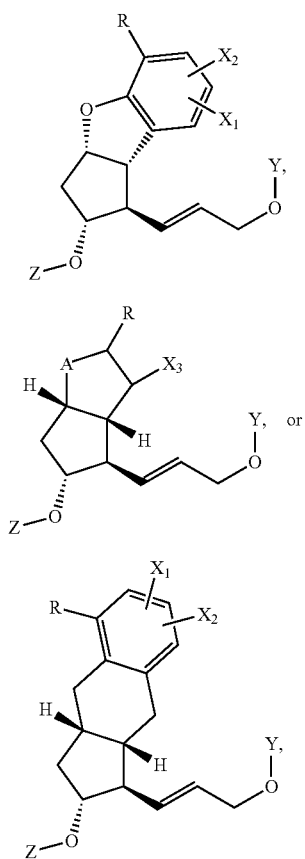

wherein R is a directly attached carboxylic acid or ester group or is a carboxylic acid or ester group attached via an aliphatic linker, optionally wherein the aliphatic linker is branched or substituted; $X_1$ and $X_2$ are independently H or an aryl group substituent; $X_3$ is H or an alkyl group substituent; A is —O—, —S—, or —CH$_2$—; and Y and Z are hydroxyl protecting groups, which can be the same or different; or a stereoisomer thereof, and wherein the hydroxyl group deprotected derivative thereof is a compound of one of formulas (V), (V'), and (V") wherein one or both of Z and Y are replaced by a hydrogen atom. In some embodiments, the compound is a compound of formula (V) or a stereoisomer and/or a hydroxyl group deprotected derivative thereof.

In some embodiments, the presently disclosed subject matter provides a method for preparing an intermediate for a synthetic prostacyclin, wherein the method comprises contacting compound A:

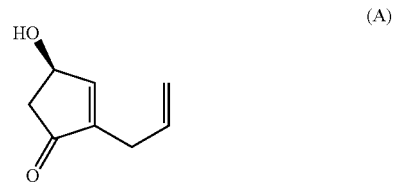

or a stereoisomer thereof with a halogenated coupling precursor molecule in a coupling reaction to provide a coupled halogenated molecule. In some embodiments, the method further comprises reacting the coupled halogenated molecule under cyclization conditions to form a cyclized molecule.

In some embodiments, the cyclized molecule is a compound of formula (II), (II') or (II"):

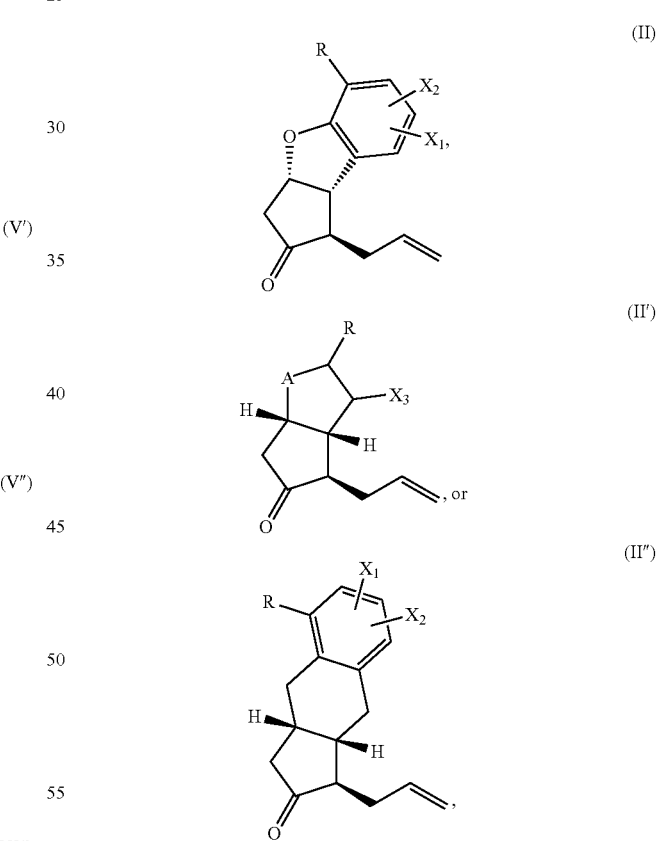

wherein R is a directly attached carboxylic acid or ester group or is a carboxylic acid or ester group attached via an aliphatic linker, optionally wherein the aliphatic linker is branched or substituted; $X_1$ and $X_2$ are independently H or an aryl group substituent; $X_3$ is H or an alkyl group substituent; and A is —O—, —S—, or —CH$_2$—; or a stereoisomer thereof.

In some embodiments, R is —CO$_2$R', —(CH$_2$)$_n$—CO$_2$R', —O—(CH$_2$)$_n$—CO$_2$R', or —CH$_2$=CH$_2$—(CH$_2$)$_n$—CO$_2$R', wherein n is an integer between 1 and 8 and R' is H, unsubstituted alkyl, substituted alkyl, aryl, or substituted aryl. In some embodiments, the cyclized molecule is a compound of formula (II). In some embodiments, the compound of formula (II) is:

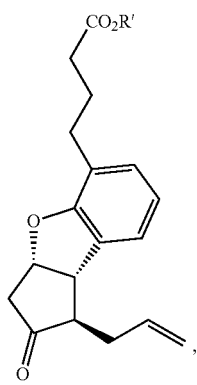

wherein R' is alkyl; or a stereoisomer thereof.

In some embodiments, the cyclization reaction is a radical type cyclization reaction.

In some embodiments, the coupled halogenated molecule is a compound of formula (I), (I'), or (I"):

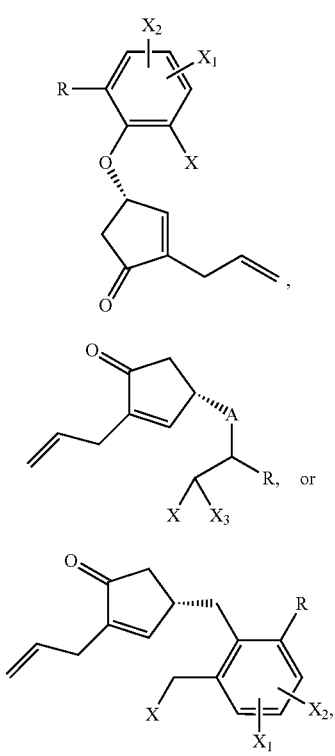

wherein R is a directly attached carboxylic acid or ester group or is a carboxylic acid or ester group attached via an aliphatic linker, optionally wherein the aliphatic linker is branched or substituted; $X_1$ and $X_2$ are independently H or an aryl group substituent; $X_3$ is H or an alkyl group substituent; A is —O—, —S—, or —$CH_2$—; and X is halo; or a stereoisomer thereof.

In some embodiments, R is —$CO_2R'$, —$(CH_2)_n$—$CO_2R'$, —O—$(CH_2)_n$—$CO_2R'$, or —$CH_2$=$CH_2$—$(CH_2)_n$—$CO_2R'$, wherein n is an integer between 1 and 8 and R' is H, unsubstituted alkyl, substituted alkyl, aryl, or substituted aryl. In some embodiments, the coupled halogenated molecule is a compound of formula (I). In some embodiments, the compound of formula (I) is

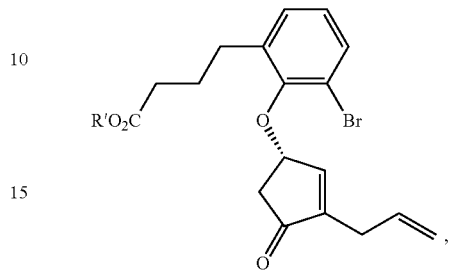

wherein R' is alkyl; or a stereoisomer thereof.

In some embodiments, the coupling reaction is a Mitsunobu-type coupling reaction.

In some embodiments, the presently disclosed subject matter provides an intermediate for a synthetic prostacyclin prepared according to the method comprising contacting compound A or a stereoisomer thereof with a halogenated coupling precursor molecule in a coupling reaction to provide a coupled halogenated molecule, optionally wherein the method further comprises reacting the coupled halogenated molecule under cyclization conditions to form a cyclized molecule. In some embodiments, the synthetic prostacyclin is a single isomer.

In some embodiments, the presently disclosed subject matter provides a compound of formula (XIV), (XIV'), or (XIV"):

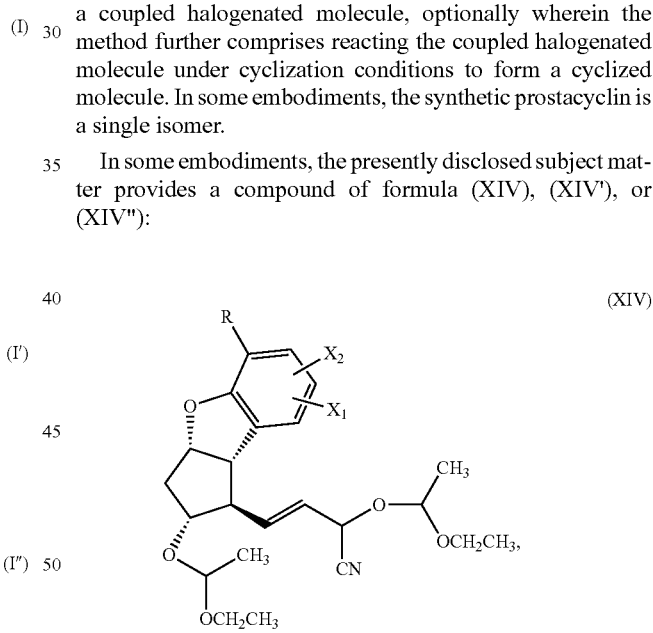

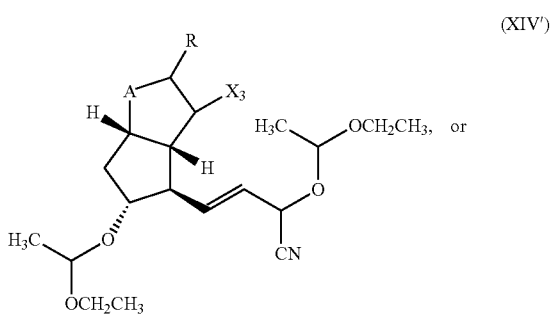

-continued

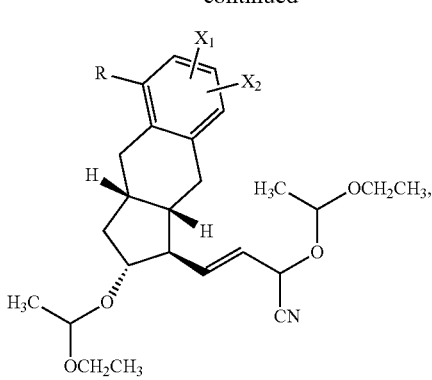

(XIV″)

wherein R is a directly attached carboxylic acid or ester group or is a carboxylic acid or ester group attached via an aliphatic linker, optionally wherein the aliphatic linker is branched or substituted; $X_1$ and $X_2$ are independently H or an aryl group substituent; $X_3$ is H or an alkyl group substituent; and A is —O—, —S—, or —CH$_2$—; or a stereoisomer thereof. In some embodiments, the compound is a compound of formula (XIV). In some embodiments, the compound of formula (XIV) is:

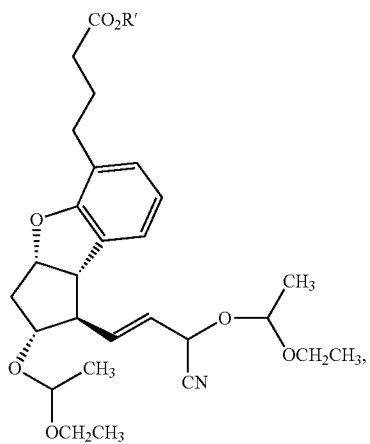

wherein R' is alkyl; or a stereoisomer thereof.

In some embodiments, the compound is a single isomer.

In some embodiments, the presently disclosed subject matter provides a method of preparing a synthetic prostacyclin, wherein the method comprises alkylating a compound of formula (XIV), (XIV'), or (XIV″).

Accordingly, it is an object of the presently disclosed subject matter to provide methods of synthesizing prostacyclins, to provide intermediates for use in these methods, and to provide single stereoisomer products of the prostacyclins.

Certain objects of the presently disclosed subject matter having been stated hereinabove, which are addressed in whole or in part by the presently disclosed subject matter, other objects and aspects will become evident as the description proceeds when taken in connection with the accompanying Examples as best described herein below.

DETAILED DESCRIPTION

The presently disclosed subject matter will now be described more fully hereinafter with reference to the accompanying Examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

By way of example and not limitation, any compound disclosed in a scheme is an aspect of the presently disclosed subject matter. Also, provided are compounds that correspond to compounds disclosed in a scheme, but which are disclosed in a specific formula instead of a scheme, merely for convenience. Further, where multi-step schemes are shown, any single step of the scheme or combination of steps of the scheme can constitute any aspect of the presently disclosed subject matter.

Unless otherwise defined, all technical and scientific terms used herein have the same meaning as commonly understood by one of ordinary skill in the art to which this presently described subject matter belongs. All publications, patent applications, patents, and other references mentioned herein are incorporated by reference in their entirety.

Throughout the specification and claims, a given chemical formula or name shall encompass all optical and stereoisomers, as well as racemic mixtures where such isomers and mixtures exist, unless otherwise noted.

I. DEFINITIONS

Following long-standing patent law convention, the terms "a", "an", and "the" refer to "one or more" when used in this application, including the claims. Thus, for example, reference to "a solvent" includes mixtures of one or more solvents, two or more solvents, and the like.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in the present specification and attached claims are approximations that can vary depending upon the desired properties sought to be obtained by the presently disclosed subject matter.

The term "about", as used herein when referring to a measurable value such as an amount of weight, molar equivalents, time, temperature, etc. is meant to encompass in one example variations of ±20% or ±10%, in another example ±5%, in another example ±1%, and in yet another example ±0.1% from the specified amount, as such variations are appropriate to perform the disclosed methods.

The term "and/or" when used to describe two or more activities, conditions, or outcomes refers to situations wherein both of the listed activities, conditions or outcomes are included or wherein only one of the two listed activities, conditions, or outcomes are included.

The term "comprising", which is synonymous with "including," "containing," or "characterized by" is inclusive or open-ended and does not exclude additional, unrecited elements or method steps. "Comprising" is a term of art used in claim language, which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

As used herein the term "alkyl" refers to $C_{1-20}$ inclusive, linear (i.e., "straight-chain"), branched, saturated or at least partially and in some cases fully unsaturated (i.e., alkenyl and alkynyl)hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms.

Alkyl groups can optionally be substituted (a "substituted alkyl") with one or more alkyl group substituents, which can be the same or different. The term "alkyl group substituent" includes but is not limited to alkyl, substituted alkyl (e.g., hydroxyl-substituted, mercapto-substituted, halo-substituted and perhalo-substituted alkyl, such as but not limited to, —$CF_3$), cycloalkyl, aryl, substituted aryl, aralkyl, halo, nitro, hydroxyl, thio, amino, carbonyl, acyl, carboxylic acid, alkoxyl, aryloxyl, and aralkoxyl. Two alkyl group substituents can together form an alkylene group (e.g., an oxy or thio containing alkylene group, such as but not limited to methylenedioxy, ethylenedioxy, propylenedioxy, ethylenedithio, etc.).

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether. Thus, examples of aryl include, but are not limited to, phenyl, naphthyl, biphenyl, and diphenylether, among others. Aryl groups include heteroaryl groups, wherein the aromatic ring or rings include a heteroatom (e.g., N, O, S, or Se). Exemplary heteroaryl groups include, but are not limited to, furanyl, pyridyl, pyrimidinyl, imidazoyl, benzimidazolyl, benzofuranyl, benzothiophenyl, quinolinyl, isoquinolinyl, and thiophenyl.

The aryl group can be optionally substituted (a "substituted aryl") with one or more aryl group substituents, which can be the same or different, wherein "aryl group substituent" includes alkyl, substituted alkyl (e.g., hydroxyalkyl, thioalkyl (or mercaptoalkyl), haloalkyl and perhaloalkyl, such as but not limited to —$CF_3$), cylcoalkyl, aryl, substituted aryl, aralkyl, amino, carboxylic acid, halo, nitro, hydroxyl, thio, acyl, alkoxyl, aryloxyl, and aralkyloxyl.

"Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$—$CH_2$—); propylene (—$(CH_2)_3$—); cyclohexylene (—$C_6H_{10}$—); —CH=CH—CH=CH—; —CH=CH—$CH_2$—; —$(CH_2)_q$—N(R)—$(CH_2)_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—$CH_2$—O—); and ethylenedioxyl (—O—$(CH_2)_2$—O—). An alkylene group can have about 2 to about 3 carbon atoms and can further have 6-20 carbons.

The term "aliphatic" refers to a group that does not include an aromatic moiety. Thus, an "aliphatic linker" can refer to an alkylene group, as in the definition of "alkylene" hereinabove.

The term "arylene" refers to a bivalent aromatic group.

As used herein, the term "acyl" refers to an organic carboxylic acid group wherein the —OH of the carboxylic acid group has been replaced with another substituent. Thus, the acyl group can be represented by RC(=O)—, wherein R is an alkyl, substituted alkyl, aralkyl, aryl or substituted aryl group as defined herein. As such, the term "acyl" specifically includes arylacyl groups, such as a phenacyl group. Specific examples of acyl groups include acetyl (Ac or —C(=O)$CH_3$) and benzoyl.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein. There can be optionally inserted along the cyclic alkyl chain one or more oxygen. Representative monocyclic cycloalkyl rings include cyclopentyl, cyclohexyl, and cycloheptyl. Multicyclic cycloalkyl rings include adamantyl, octahydronaphthyl, decalin, camphane, and noradamantyl.

"Alkoxyl" refers to an alkyl-O— group wherein alkyl is as previously described. The term "alkoxyl" as used herein can refer to, for example, methoxyl, ethoxyl, propoxyl, isopropoxyl, butoxyl, t-butoxyl, and pentoxyl. The term "oxyalkyl" can be used interchangably with "alkoxyl".

"Aryloxyl" refers to an aryl-O— group wherein the aryl group is as previously described, including a substituted aryl. The term "aryloxyl" as used herein can refer to phenyloxyl or hexyloxyl, and to alkyl, substituted alkyl, or alkoxyl substituted phenyloxyl or hexyloxyl.

"Aralkyl" refers to an -aryl-alky or an -alkyl-aryl group wherein aryl and alkyl are as previously described, and included substituted aryl and substituted alkyl. Exemplary aralkyl groups include benzyl, phenylethyl, and naphthylmethyl.

"Aralkyloxyl" or "aralkoxyl" refer to an aralkyl-O— group wherein the aralkyl group is as previously described. An exemplary aralkyloxyl group is benzyloxyl.

The term "carbonyl" refers to the group —C(=O)—. The term "carbonyl carbon" refers to a carbon atom of a carbonyl group. Other groups such as, but not limited to, acyl groups, anhydrides, aldehydes, esters, lactones, amides, ketones, carbonates, and carboxylic acids, include a carbonyl group. The terms "carboxylic acid" and "carboxylic acid group" as used herein can refer to the group —C(=O)OH.

The terms "halo", "halide", or "halogen" as used herein refer to fluoro, chloro, bromo, and iodo groups.

The term "amine" refers to a molecule having the formula $N(R)_3$, or a protonated form thereof, wherein each R is independently H, alkyl, substituted alkyl, aryl, substituted aryl, or aralkyl or wherein two R groups together form an alkylene or arylene group. The term "primary amine" refers to an amine wherein at least two R groups are H. The term "secondary amine" refers to an amine wherein only one R group is H. The term "alkylamine" refers to an amine wherein two R groups are H and the other R group is alkyl or substituted alkyl. "Dialkylamine" refers to an amine where two R groups are alkyl. "Arylamine" refers to an amine wherein one R group is aryl. Amines can also be protonated, i.e., have the formula $[NH(R)_3]^+$.

The term "amino" refers to the group —$N(R)_2$ wherein each R is independently H, alkyl, substituted alkyl, aryl, substituted aryl, or aralkyl.

The terms "hydroxyl" or "hydroxyl" refer to the —OH group.

The term "secondary alcohol" refers to a —CH(OH)— group. The term "primary alcohol" refers to the group —$CH_2OH$.

The terms "thio" or "mercapto" refer to the —SH group.

The term "hydroxyl protecting group" refers to groups that are known in the art of organic synthesis for masking hydroxyl groups during chemical group transformations elsewhere in the molecule. Accordingly, hydroxyl protecting groups are groups that can replace the hydrogen atom of a hydroxy group on a molecule and that are stable and non-reactive to reaction conditions to which the protected molecule is to be exposed. Suitable hydroxyl protecting groups are described, for example, in Greene and Wuts, Protective Groups in Organic Synthesis, 3$^{rd}$ Edition; New York, John Wiley & Sons, Inc., 1999. Hydroxyl protecting groups include, but are not limited to, groups that can be reacted with hydroxyl groups, or bonded to the oxygen atom of the hydroxyl groups, to form ethers, such as silyl ethers (e.g., trimethylsilyl (TMS), triethylsilyl (TES), tert-butyldimethylsilyl (TBDMS), t-butyldiphenylsilyl (TBDPS), or phenyldimethylsilyl ethers) substituted methyl ethers (e.g., methoxymethyl (MOM), benzyloxymethyl (BOM), tetrahydropyranyl (THP)), substituted ethyl ethers, benzyl ethers and substituted benzyl ethers; esters (e.g., acetate, formate, chloroacetate); and carbonates. For example, in some embodiments, the hydroxyl protecting group is an acyl group that can form an ester with the oxygen atom from the hydroxyl group (e.g., —C(=O)R, wherein R is alkyl, substituted alkyl, aralkyl, aryl or substituted aryl). In some embodiments, the hydroxyl protecting group is —C(=O)$CH_3$ (Ac), —C(=O)H, —C(=O)$CH_2$Cl, —C(=O)$C_6H_5$, or —C(=O)$CH_2C_6H_5$ (Bz).

The term "silyl" refers to groups comprising silicon atoms (Si). In some embodiments, the term silyl refers to the group —$Si(R)_3$, wherein each R is independently alkyl, substituted alkyl, aralkyl, aryl, and substituted aryl. In some embodiments, the term silyl refers to a trialkylsilyl group.

As used herein, the terms "siloxy" and "silyl ether" refer to groups or compounds including a silicon-oxygen (Si—OR) bond and wherein R is an organic group, such as an alkyl or aryl group (i.e., methyl, ethyl, phenyl, etc.).

The term "aprotic solvent" refers to a solvent molecule which can neither accept nor donate a proton. Examples of aprotic solvents include, but are not limited to, ethyl acetate; carbon disulphide; ethers, such as, diethyl ether, tetrahydrofuran (THF), ethylene glycol dimethyl ether, dibutyl ether, diphenyl ether, MTBE, and the like; aliphatic hydrocarbons, such as hexane, pentane, cyclohexane, and the like; aromatic hydrocarbons, such as benzene, toluene, naphthalene, anisole, xylene, mesitylene, and the like; and symmetrical halogenated hydrocarbons, such as carbon tetrachloride, tetrachloroethane, and dichloromethane. Additional aprotic solvents include, for example, acetone, acetonitrile, butanone, butyronitrile, chlorobenzene, chloroform, 1,2-dichloroethane, dimethylacetamide, N,N-dimethylformamide (DMF), dimethylsulfoxide (DMSO), and 1,4-dioxane.

The term "protic solvent" refers to a solvent molecule which contains a hydrogen atom bonded to an electronegative atom, such as an oxygen atom or a nitrogen atom. Typical protic solvents include, but are not limited to, carboxylic acids, such as acetic acid, alcohols, such as methanol and ethanol, amines, amides, and water. The general term "solvent" can refer to either protic or nonprotic solvents, as well as mixtures thereof.

II. GENERAL CONSIDERATIONS

The presently disclosed subject matter provides, in some embodiments, methods of preparing synthetic prostacyclins, including methods of preparing racemic or single isomer synthetic prostacyclins or their synthetic intermediates. Also provided are the compounds themselves. The term "synthetic prostacyclins" as used herein can refer to any prostacyclin that can be prepared via synthetic organic chemistry, including those prostacyclins that are also naturally occurring, such as Prostacyclin (PGI$_2$):

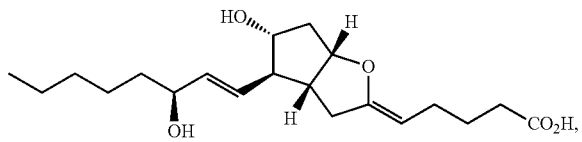 [SMILES: CCCCC[C@H](O)/C=C/[C@@H]1[C@H]2C/C(=C/CCCC(=O)O)O[C@H]2C[C@H]1O]

which is also known as Epopreostenol.

Thus, examples of synthetic prostacyclins include, but are not limited to: Prostacyclin, Carbaprostacyclin, which has the structure:

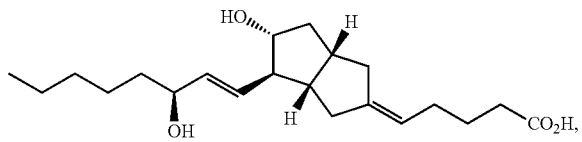 [SMILES: CCCCC[C@H](O)/C=C/[C@@H]1[C@H]2C/C(=C/CCCC(=O)O)C[C@H]2C[C@H]1O]

Iloprost, which has the structure:

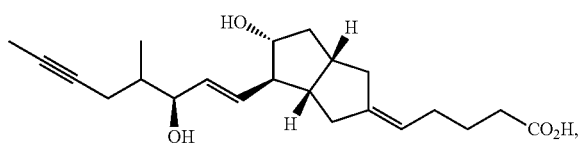 [SMILES: CC#CCC(C)[C@H](O)/C=C/[C@@H]1[C@H]2C/C(=C/CCCC(=O)O)C[C@H]2C[C@H]1O]

Icaprost, which has the structure:

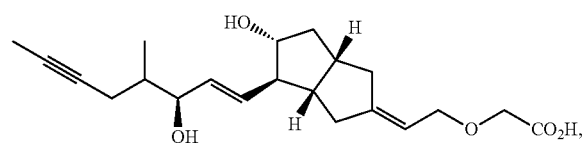 [SMILES: CC#CCC(C)[C@H](O)/C=C/[C@@H]1[C@H]2C/C(=C/COCC(=O)O)C[C@H]2C[C@H]1O]

Treprostinil (also known as Rumodolin), which has the structure:

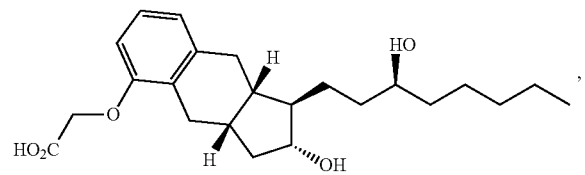 [SMILES: CCCCC[C@H](O)CC[C@@H]1[C@H]2Cc3cccc(OCC(=O)O)c3C[C@H]2C[C@H]1O]

and

Beraprost, which has the structure:

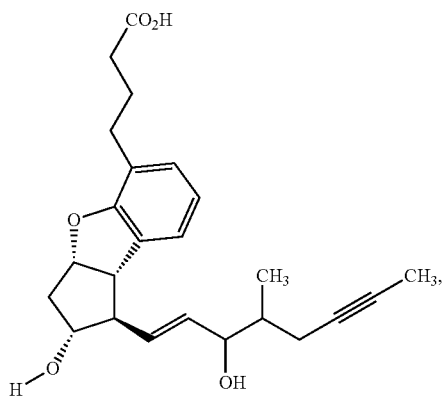 [SMILES: CC#CCC(C)C(O)/C=C/[C@@H]1[C@H]2c3cccc(CCCC(=O)O)c3O[C@H]2C[C@H]1O]

as well as the esters, stereoisomers, and salts thereof, or other analogues or derivatives of the recited synthetic prostacyclins, such as compounds comprising other aliphatic linker groups linking the carboxylic acid group to the cyclic components of the synthetic prostacyclins, compounds containing additional alkene and/or alkyne bonds, and/or compounds containing additional substituents on the cyclic components of the synthetic prostacyclins.

In some embodiments, the synthetic prostacyclin is Beraprost or an analogue thereof having the structure:

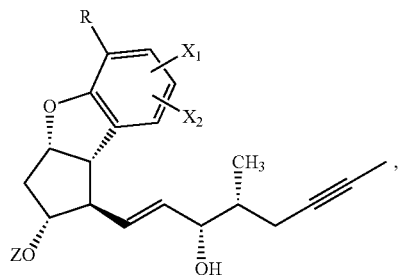

wherein:

R is a directly attached carboxylic acid or ester group or is a carboxylic acid or ester group attached via an aliphatic linker, optionally wherein the aliphatic linker is branched or substituted (i.e., with an alkyl group substituent);

$X_1$ and $X_2$ are independently H or an aryl group substituent, such as, but not limited to alkyl, substituted alkyl (e.g., hydroxyl- or thioalkyl), OH, SH, alkoxy, alkylthio, aryl, or substituted aryl; and Z is H or a hydroxyl protecting group (e.g., —C(=O)CH$_3$ or another acyl group); or a salt or stereoisomer thereof.

Thus, R can be —CO$_2$R' (i.e., a directly attached ester or carboxylic acid) or -alkylene-CO$_2$R' (i.e., aliphatic ester or carboxylic acid), wherein R' is H, unsubstituted alkyl (e.g., lower alkyl, such as methyl, ethyl, n-propyl, isopropyl, n-butyl, tert-butyl, n-pentyl, or n-hexyl), substituted alkyl, aralkyl, aryl, or substituted aryl, optionally wherein the alkylene can be branched, include a carbon-carbon double bond, and/or include an ether linkage. In some embodiments, R is —CO$_2$R' or —(CH$_2$)$_n$—CO$_2$R', wherein n is an integer from 1 to 8 (i.e., 1, 2, 3, 4, 5, 6, 7, or 8). In some embodiments, R is —(CH$_2$)$_n$—CO$_2$R', n is 3, and R' is H or methyl.

In some embodiments, $X_1$ and $X_2$ are both H.

In some embodiments, the presently disclosed subject matter provides compounds that can be used as synthetic intermediates for the synthesis of synthetic prostacyclins (e.g., for the synthesis of single isomer (e.g., single stereoisomer) synthetic prostacyclins), such as, but not limited to Beraprost. By "single isomer" it is meant that the synthesis provides a compound wherein within any mixture of stereoisomers of that compound there is at least 90, 91, 92, 93, 94, 95, 96, 97, 98, 99, or 99.5% of a single particular stereoisomer. In some embodiments, essentially only one single particular stereoisomer is produced. In some embodiments, the single isomer is the particular stereoisomer that is indicated in a formula structure. In some embodiments, the single isomer is a different stereoisomer than that indicated in the formula structure.

II.A. Intermediates for Preparing Synthetic Prostacyclins

In some embodiments, the presently disclosed subject matter (including the presently disclosed methods involving the use thereof) provides a synthetic intermediate of one of formulas (V), (V') or (V"):

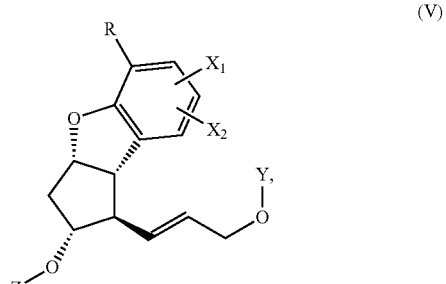

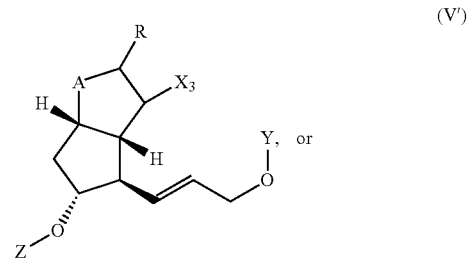

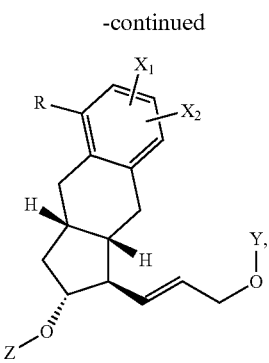

(V″)

wherein:

R is a directly attached carboxylic acid or ester group or is a carboxylic acid or ester group attached via an aliphatic linker, optionally wherein the aliphatic linker is branched or substituted;

$X_1$ and $X_2$ are independently H or an aryl group substituent;

$X_3$ is H or an alkyl group substituent;

A is —O—, —S—, or —CH$_2$—; and

Y and Z are hydroxyl protecting groups, which can be the same or different; or a stereoisomer and/or hydroxyl group deprotected derivative thereof, and wherein the hydroxyl group deprotected derivative thereof is a compound of one of formulas (V), (V′), and (V″) wherein one or both of Z and Y are replaced by a hydrogen atom.

In some embodiments, the synthetic intermediate of formula (V) can be prepared as shown in Scheme 1, below. For example, as shown in Scheme 1, the synthesis of the compound of formula (V) and other related synthetic intermediates for prostacyclins can be performed by coupling compound A or its stereoisomer with a halophenol such as bromophenol B that further comprises a group R, e.g., a directly attached ester or an ester attached via an aliphatic linker. In some embodiments, the coupling reaction is a Mitsunobu-type coupling reaction performed in the presence of triphenylphosphine (or any alkyl substituted triphenylphosphine, such as, but not limited to, tri-p-tolylphosphine) and an azodicarboxylate (e.g., diethyl azodicarboxylate (DEAD) or diisopropyl azodicarboxylate (DIAD)). The Mitsunobu-type coupling reaction can be performed in any suitable aprotic solvent, such as, but not limited to toluene, dioxane or THF, at any suitable temperature (e.g., between −70° C. and 50° C.). The coupling reaction can result in an ether linkage between the cyclopentenone ring of A and the aryl group of compound B.

The product of the coupling reaction (i.e., compound 1′) can be cyclized to compound 2′, e.g., via a radical initiated cyclization reaction, and then the ketone of compound 2′ can be reduced to secondary alcohol 3′ using any suitable carbonyl reducing agent. For example, the reducing agent can be a hydride donor (e.g., lithium aluminum hydride (LAH) or DIBAL), particularly those that can reduce a ketone relatively rapidly in comparison to a carboxylic acid or ester. In some embodiments, the reducing agent can be, but is not limited to, sodium borohydride (NaBH$_4$), B$_2$H$_6$, or LiAlH[OC(CH$_3$)$_3$]$_3$. The reduction can be performed in any suitable solvent, e.g., THF, methanol, or ethanol. In some embodiments, the radical initiated cyclization reaction can be performed in the presence of an alkyl tin hydride, such as, but not limited to, trihexyltinhydride or tributyltinhydride, and a radical initiator, such as AIBN or benzoyl peroxide. Suitable solvents for the cyclization reaction include, but are not limited to, benzene and toluene.

The secondary alcohol of compound 3′ can be protected by any suitable protecting group to form compound 4′. For example, suitable hydroxyl protecting groups include, but are not limited to, silyl protecting groups (e.g., TMS, TES, TBDMS, TBDPS, and phenyldimethylsilyl); substituted methyl ethers (e.g., MOM, BOM, and THP); substituted ethyl ethers (e.g., 1-ethoxyethylether); benzyl and substituted benzyl; acyl (e.g., —C(=O)R, wherein R is alkyl or substituted alkyl; and carbonates. In some embodiments, the hydroxyl protecting group is a substituted methyl ether, a substituted ethyl ether, or an acyl group. In some embodiments, the hydroxyl protecting group is an acyl group. In some embodiments, Z is Ac (i.e., —C(=O)CH$_3$). When the protecting group is Ac, compound 3′ can be protected using any suitable acylating agent, such as, but not limited to acetyl chloride or Ac$_2$O, in the presence of a non-nucleophilic base, such as, but not limited to triethylamine, pyridine, or dimethylaminopyridine (DMAP). The protection can be performed in any suitable aprotic solvent, such as, but not limited to dichloromethane, THF, or toluene.

Compound 4′ or compound 3′ can undergo oxidative rearrangement, e.g., in the presence of a palladium (II) catalyst, such as PdCl$_2$ or palladium acetate, to form compound 5′ (i.e., a compound of Formula (V)) or compound 5″. The rearrangement can be performed in any suitable solvent (e.g., DMF, NMP, DMA, etc.), at an oxygen pressure range between 1 and 150 psi, at any suitable temperature (e.g., between 20° C. and 200° C.).

Ozonolysis to provide an aldehyde, followed by reduction of the aldehyde can provide compound 6′ or 7′. The ozonolysis reaction can be performed in any suitable solvent or solvent mixture (e.g., a mixture of dichloromethane and methanol or ethanol). Deprotection of the secondary alcohol can be performed via any suitable method, depending upon the identity of the protecting group. When the protecting group is Ac, any strong acid can be used in the deprotection step, such as, but not limited to, hydrochloric acid, PTSA, MSA, or sulfuric acid. The deprotection step can be performed at any suitable temperature (e.g., between about 0° C. and about 100° C.). Reduction of the aldehyde can be performed using any suitable carbonyl reducing agent, e.g., a hydride donor, such as, but not limited to, sodium borohydride (NaBH$_4$), B$_2$H$_6$, or LiAlH[OC(CH$_3$)$_3$]$_3$.

Scheme 1. Synthesis of Synthetic Prostacyclin Intermediates.

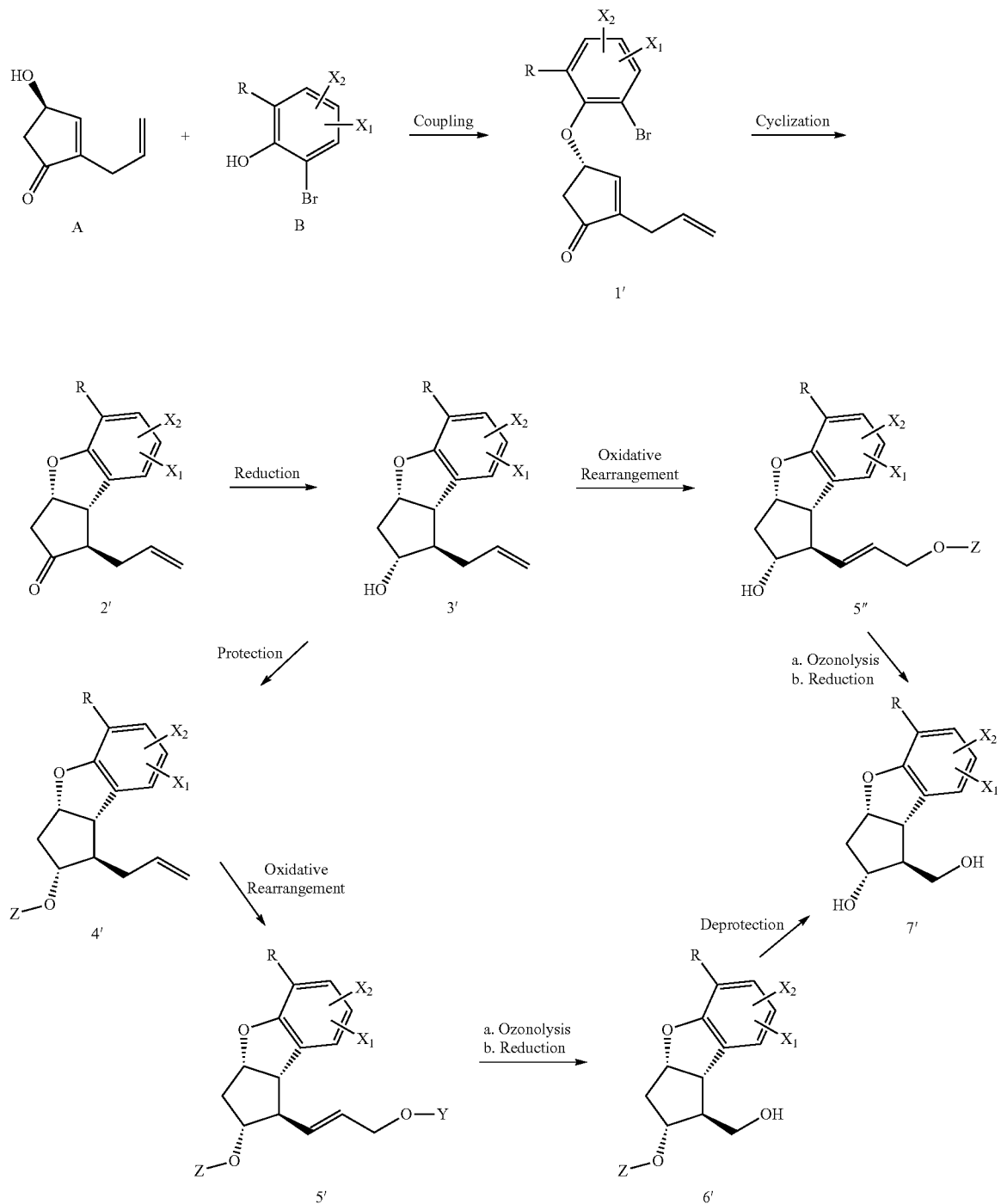

The synthesis of intermediates for prostacyclins with different cyclic core structures other than that of Formula (V) (e.g., other than that of Beraprost) can be prepared via analogous routes, but using different starting materials in the initial coupling reaction. For example, different compounds can be used in place of starting material B to provide coupled halogenated molecules analogous to compound 1' that can be cyclized (e.g., via radical initiated cyclization) to provide cyclized compounds analogous to compound 2', but having cyclic core structures of synthetic prostacyclins such as Carboprostacyclin, $PGI_2$, Iloprost, Icaprost, or Treprostinil. See e.g., Formulae (II') and (II''), hereinbelow.

For example, to provide synthetic prostacyclins such as Carbaprostacyclin, $PGI_2$, Iloprost, or Icaprost, or their analogues, the coupled halogenated molecule can have a structure such as:

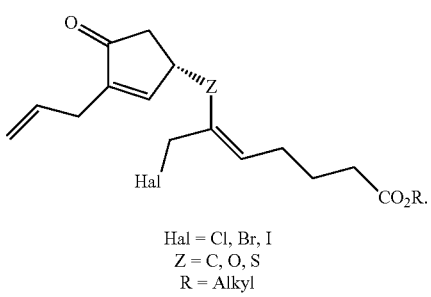

Hal = Cl, Br, I
Z = C, O, S
R = Alkyl

To provide synthetic prostacyclins such as Treprostinil, or an analogue thereof, the coupled halogenated molecule can have a structure such as:

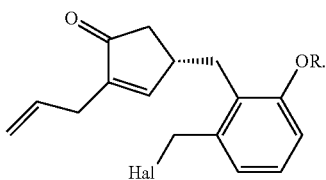

Thus, for instance, in some embodiments, the presently disclosed subject matter provides a method for preparing an intermediate for a synthetic prostacyclin, wherein the method comprises contacting a compound A or a stereoisomer or analogue thereof with a halogenated coupling precursor molecule in a coupling reaction to provide a coupled halogenated precursor molecule. The method can further comprise reacting the coupled halogenated molecule under cyclization conditions to form a cyclized molecule. In some embodiments, the coupling reaction is a Mitsunobu coupling reaction. In some embodiments, the cyclization reaction is a radical initiated cyclization reaction.

In some embodiments, the cyclized molecule is a compound of formula (II), (II') or (II''):

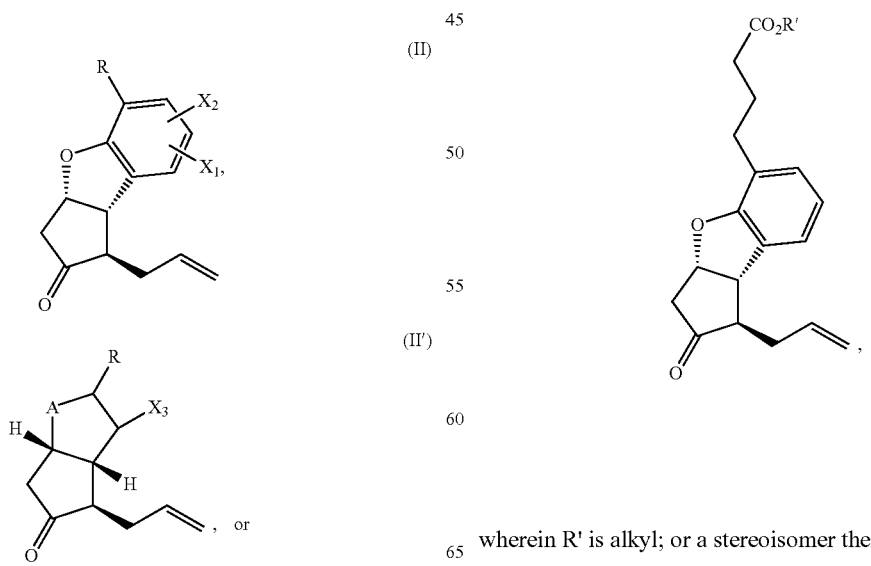

wherein R is a directly attached carboxylic acid or ester group or is a carboxylic acid or ester group attached via an aliphatic linker, optionally wherein the aliphatic linker is branched or substituted; $X_1$ and $X_2$ are independently H or an aryl group substituent; $X_3$ is H or an alkyl group substituent; and A is —O—, —S—, or —CH$_2$—; or a stereoisomer thereof. In some embodiments, R is —CO$_2$R', —(CH$_2$)$_n$—CO$_2$R', —O—(CH$_2$)$_n$—CO$_2$R', or —CH$_2$=CH$_2$—(CH$_2$)$_n$—CO$_2$R', wherein n is an integer between 1 and 8 and R' is H, unsubstituted alkyl, substituted alkyl, aryl, or substituted aryl. In some embodiments, R' is alkyl.

For use in the synthesis of Beraprost or an analogue thereof (e.g., when the compound is a compound of formula (II)), R can be —(CH$_2$)$_n$—CO$_2$R'. For the synthesis of PGI$_2$, Carbaprostacyclin, Iloprost, or Icaprost, or their analogues (e.g., when the compound is a compound of formula (II')), R can be —CH$_2$=CH$_2$—(CH$_2$)$_n$—CO$_2$R'. For the synthesis of Treprostinil or analogues thereof (e.g., when the compound is a compound of formula (II'')), R can be —O—(CH$_2$)$_n$—CO$_2$R'.

In some embodiments, the cyclized molecule is a compound of formula (II) or a stereoisomer thereof. In some embodiments, the compound of formula (II) is

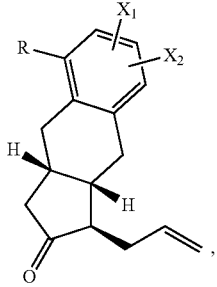

wherein R' is alkyl; or a stereoisomer thereof.

In some embodiments, the coupled halogenated molecule is a compound of formula (I), (I'), or (I''):

25

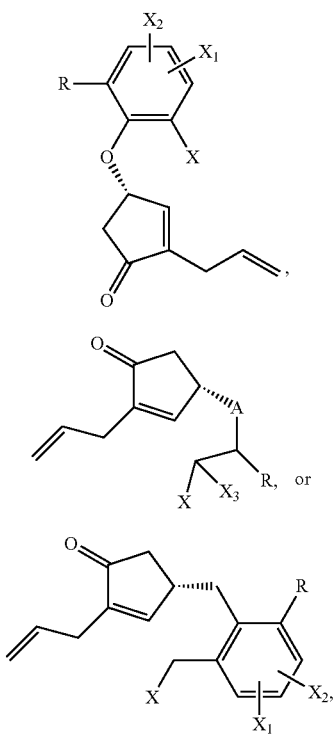

wherein R is a directly attached carboxylic acid or ester group or is a carboxylic acid or ester group attached via an aliphatic linker, optionally wherein the aliphatic linker is branched or substituted; $X_1$ and $X_2$ are independently H or an aryl group substituent; $X_3$ is H or an alkyl group substituent; A is —O—, —S—, or —$CH_2$—; and X is halo; or a stereoisomer thereof.

In some embodiments, R is —$CO_2R'$, —$(CH_2)_n$—$CO_2R'$, —O—$(CH_2)_n$—$CO_2R'$, or —$CH_2$=$CH_2$—$(CH_2)_n$—$CO_2R'$, wherein n is an integer between 1 and 8 and R' is H, unsubstituted alkyl, substituted alkyl, aryl, or substituted aryl. In some embodiments, the R of the compound of formula (I) is —$(CH_2)_n$—$CO_2R'$. In some embodiments, R of the compound of formula (I') is —$CH_2$=$CH_2$—$(CH_2)_n$—$CO_2R'$. In some embodiments, R of the compound of formula (I'') is —O—$(CH_2)_n$—$CO_2R'$. In some embodiments, R' is alkyl (e.g., methyl). In some embodiments, X is Cl, Br, or I. In some embodiments, X is Br.

In some embodiments, the coupled halogenated molecule is a compound of formula (I) or a stereoisomer thereof. In some embodiments, the compound of formula (I) is

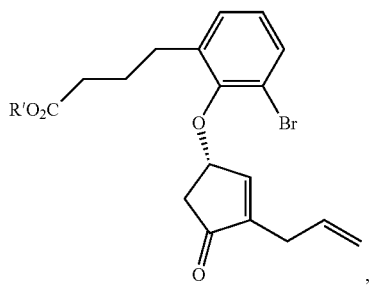

wherein R' is alkyl; or a stereoisomer thereof.

26

II.B. Synthetic Prostacyclins Via Horner-Emmons Reaction.

The intermediates of Formulas (V), (V'), and (V'') can be transformed into synthetic prostacyclins by various additional synthetic sequences. In some embodiments, the compounds of Formula (V), (V'), of (V'') can be transformed into a synthetic prostacyclin or other synthetic intermediate thereof via a series of reactions involving a Horner-Emmons reaction of a enantiomerically pure phosphonate C and an aldehyde (e.g., such as the aldehyde produced by the ozonolysis of the compound of formula (V), (V'), or (V'')).

For example, as shown in Scheme 2, ozonolysis of compound 5' can produce aldehyde 9'. The ozonolysis reaction can be performed in any suitable solvent or mixture of solvents (e.g., dichloromethane and ethanol or methanol). Aldehyde 9' can be reacted with C under Horner-Emmons conditions (e.g., in the presence of sodium hydride or another strong base, such as but not limited to, NaHMDS, KHMDS, or t-BuOK, that can deprotonate the phosphonate to provide a phosphonate carbanion) to provide compound 10'. The Horner-Emmons reaction can be performed in any suitable aprotic solvent, e.g., dimethylether, THF, or toluene.

The ketone of compound 10' can be stereoselectively reduced to a hydroxyl group, and the hydroxyl protecting group Z can be removed, if desired, to provide compound 11', i.e., Beraprost or an analogue thereof. Exemplary stereoselective reducing agents for the reduction of the ketone of compound 10' include, but are not limited to Corey-Bakshi-Shibata (CBS) catalysts (e.g., oxazaborolidine proline derivatives). The reduction reaction can take place in the presence of a $BH_3$ source, e.g., $BH_3$.THF or $BH_3$ dimethylsulfide complex. The reaction can take place in any suitable aprotic solvent, e.g., THF or dioxane. The deprotection reaction can be performed using any suitable alkaline hydroxide, e.g., NaOH, LiOH, KOH, or CsOH.

Scheme 2. Synthesis of Synthetic
Prostacyclins Using Horner-Emmons Reaction.

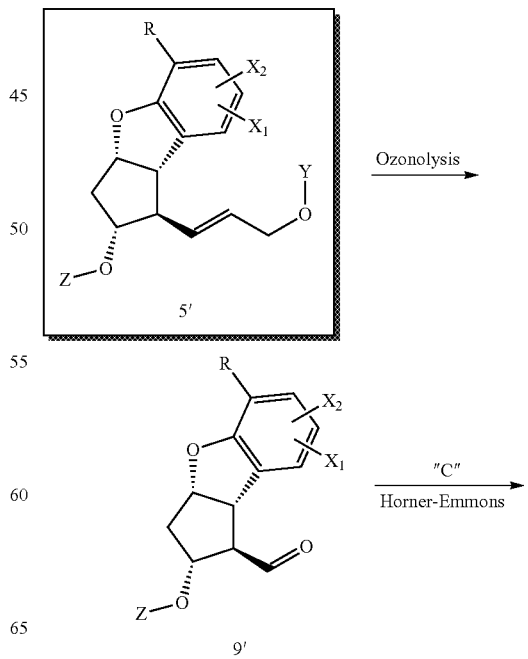

27
-continued

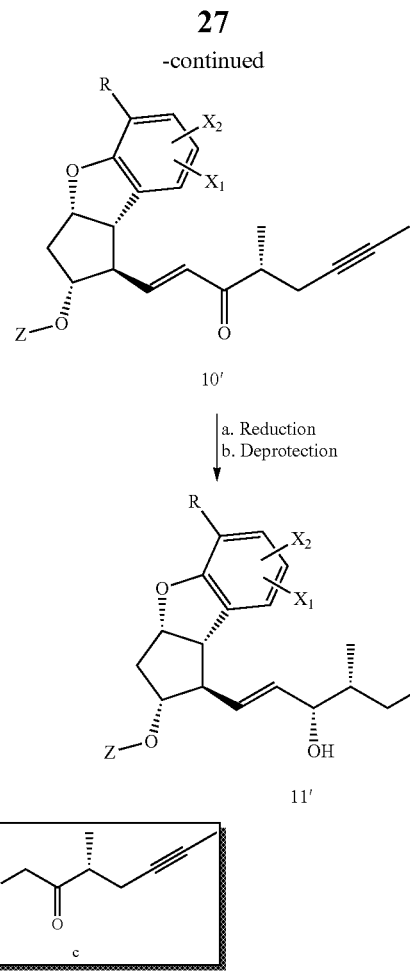

28
-continued

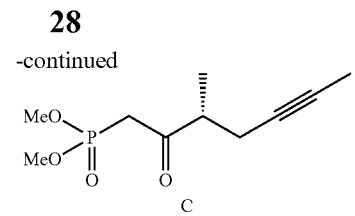

Using the synthesis routes outlined in Schemes 1-3, all eight isomers of, Beraprost can be provided by appropriate combination of (a) isomer of compound A, (b) isomer of compound C, and (c) stereoselective reducing agent. Table 1 shows the outcome of the various combinations of A, C, and isomer of CBS catalyst.

TABLE 1

Combinations of Reagents Leading to Eight Isomers of Beraprost.

| Isomer of compound A | Isomer of compound C | Isomer of CBS | Beraprost isomer |
| --- | --- | --- | --- |
| R | R | R | |
| R | R | S | |
| R | S | R | |
| R | S | S | |

Enantiomerically pure C can be synthesized as shown in Scheme 3. For example, racemic compound 16' can be resolved (e.g., via classical resolution, such as by crystallization, a resolution of diastereomers, or a kinetic resolution using enzyme technology) to provide enantiomerically pure carboxylic acid 17' or ester 18' (either as the stereoisomer shown or the other stereoisomer). The resulting compound can then be reacted with a dialkyl alkylphosphonate (e.g., dimethyl methylphosphonate (DMMP)) in the presence of a base to provide compound C.

Scheme 3. Synthesis of Enantiomerically Pure C.

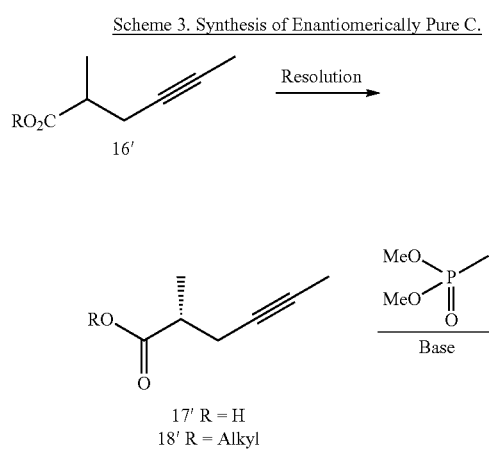

TABLE 1-continued

Combinations of Reagents Leading to Eight Isomers of Beraprost.

| Isomer of compound A | Isomer of compound C | Isomer of CBS | Beraprost isomer |
|---|---|---|---|
| S | R | R | HO₂C ... |
| S | R | S | HO₂C ... |
| S | S | R | HO₂C ... |
| S | S | S | HO₂C ... |

Accordingly, in some embodiments, the presently disclosed subject matter provides a method for preparing a synthetic prostacyclin or a synthetic intermediate thereof, wherein the method comprises contacting an aldehyde with an enantiomerically pure phosphonate in a Horner-Emmons reaction to provide an alkene. In some embodiments, the alkene can be a hydroxyl protected derivative of a compound of formula (Xb), (Xb') or (Xb") as described herein below (e.g. the compound can also contain a ketone group). The synthetic prostacyclin or synthetic intermediate thereof can be provided as a single isomer or as a racemic mixture.

In some embodiments, the aldehyde is a product of the ozonolysis of a compound of formula (V), (V') or (V") or a stereoisomer thereof. In some embodiments, R for these formulae can be —CO₂R', —(CH₂)$_n$—CO₂R', —O—(CH₂)$_n$—CO₂R', or —CH₂=CH₂—(CH₂)$_n$—CO₂R', wherein n is an integer between 1 and 8 and R' is H, unsubstituted alkyl, substituted alkyl, aryl, or substituted aryl. In some embodiments, Y and Z are each acyl. In some embodiments, Y and Z are each —C(=O)CH₃. In some embodiments, the aldehyde is the product of the ozonolysis of a compound of formula (V) or a stereoisomer thereof. In some embodiments, the aldehyde is the product of the ozonolysis of the compound:

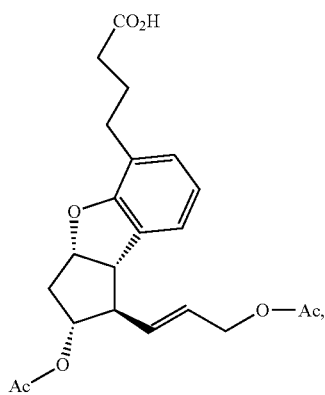 [SMILES: CC(=O)OC/C=C/[C@@H]1[C@H]2c3cccc(CCCC(=O)O)c3O[C@H]2C[C@H]1OC(C)=O]

or a stereoisomer thereof.

In some embodiments, the enantiomerically pure phosphonate has a structure:

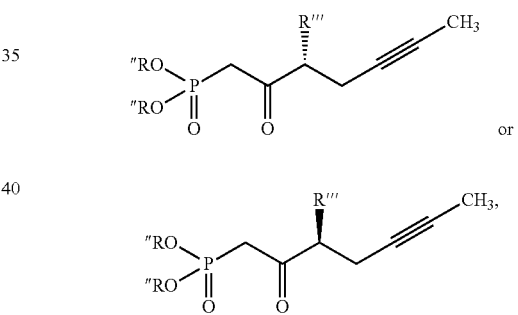

wherein R" and R'" are alkyl. In some embodiments, R" is methyl. In some embodiments, R" is methyl.

In some embodiments, the method comprises or further comprises stereoselectively reducing a ketone in the alkene compound formed during the Horner-Emmons reaction. In some embodiments, the stereoselective reduction is performed using a Corey-Bakshi-Shibata (CBS) catalyst. In some embodiments, the method further comprises deprotecting protected hydroxyl groups. In some embodiments, the synthetic prostacyclin is Beraprost (e.g., a single isomer of Beraprost).

II.C. Synthetic Prostacyclins Via Compounds of Formulas (XIV), (XIV'), and (XIV").

The compounds of formulas (V), (V'), and (V") can also be used to provide synthetic prostacyclins or their synthetic intermediates (including single isomers thereof) according to the synthetic route as shown in Scheme 4, below, or one analogous thereto, via a compound of formula (XIV), (XIV'), or (XIV"):

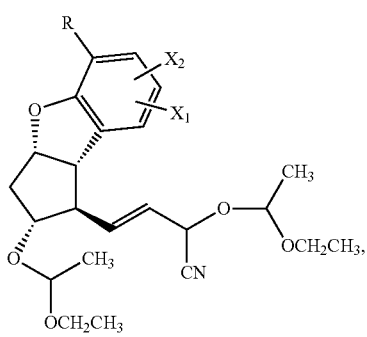

(XIV)

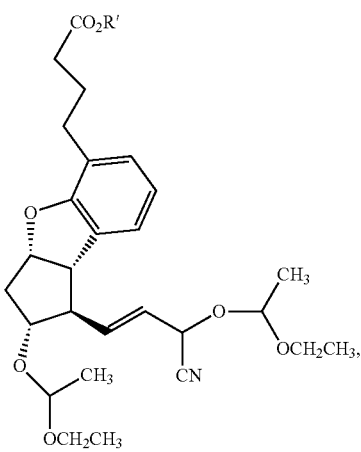

(XIV')

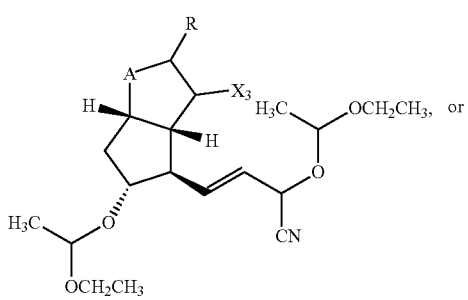

or

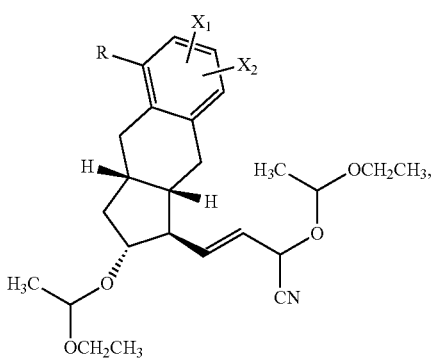

(XIV")

wherein R is a directly attached carboxylic acid or ester group or is a carboxylic acid or ester group attached via an aliphatic linker, optionally wherein the aliphatic linker is branched or substituted; $X_1$ and $X_2$ are independently H or an aryl group substituent; $X_3$ is H or an alkyl group substituent; and A is —O—, —S—, or —$CH_2$—; or a stereoisomer thereof.

In some embodiments, the compound of formula (XIV) is a compound wherein R is —$(CH_2)_n$—$CO_2R'$, wherein n is an integer between 1 and 8 and R' is alkyl or a stereoisomer thereof. In some embodiments, the compound of formula (XIV) is:

wherein R' is alkyl; or a stereoisomer thereof.

In some embodiments, the compound of formula (XIV), (XIV') or (XIV") is a single isomer (i.e., a single stereoisomer). In some embodiments, the presently disclosed subject matter provides a compound of formula (XIV), (XIV'), or (XIV").

In some embodiments, a compound of formula (V), (V') or (V"), such as compound 5', which is a compound of formula (V), can be deprotected (e.g., both hydroxyl protecting groups can be removed) under suitable conditions. One of ordinary skill in the art would appreciate that deprotection conditions vary depending upon the identity of the protecting group. Suitable conditions can be found, for example in Greene and Wuts, Protective Groups in Organic Synthesis, $3^{rd}$ Edition; New York, John Wiley & Sons, Inc., 1999.

Following deprotection of 5' to form 12', the primary alcohol can be selectively oxidized to form aldehyde 13'. The oxidation can be performed in any suitable solvent, e.g., dichloromethane or THF. Protection of both the aldehyde carbonyl and remaining secondary alcohol (for example so that the aldehyde carbonyl is protected as an O-1-ethoxyethyl cyanohydrin and the alcohol as a 1-ethoxyethyl ether) provides protected intermediate 14'. In some embodiments, the protection reaction reagents include ethyl vinyl ether and a metal cyanide, such as but not limited to NaCN or KCN. The protection reaction can be performed in any suitable aprotic solvent, e.g., DME or THF. Compound 14' can be alkylated with a haloalkyne 19' in the presence of a strong base (e.g., LDA, NaHMDS, KHMDS) in any suitable aprotic solvent to provide alkylated compound 15', which can be fully deprotected using any suitable reagents to provide ketone 10b' (e.g., via hydrolysis of the ether and cyanohydrin). In some embodiments, the deprotection is performed using a strong acid, such as, but not limited to, sulfuric acid, hydrochloric acid, TFA, or PTSA. The ketone can be stereoselectively reduced to provide compound 11b'.

Scheme 4. Synthesis of Synthetic Prostacyclins Via Alkylation of Protected Cyanohydrin.

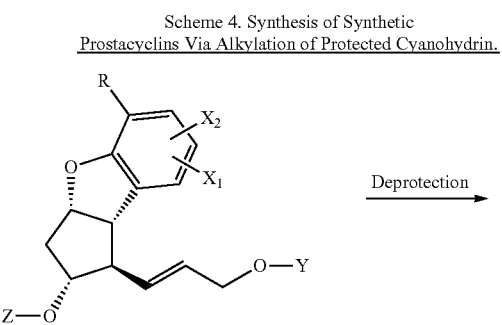

5'

Deprotection →

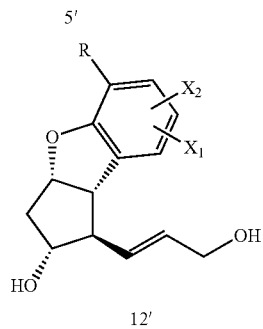

12'

Oxidation →

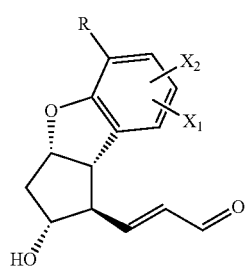

13'

Protection →

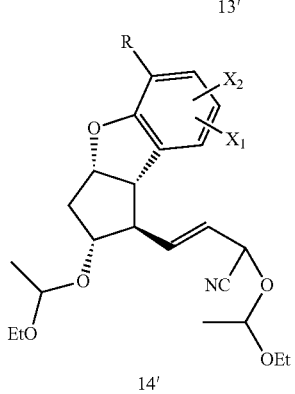

14'

Alkylation →

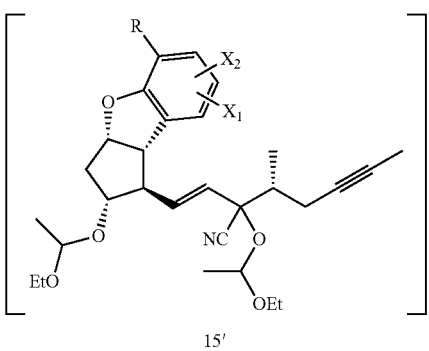

15'

Hydrolysis →

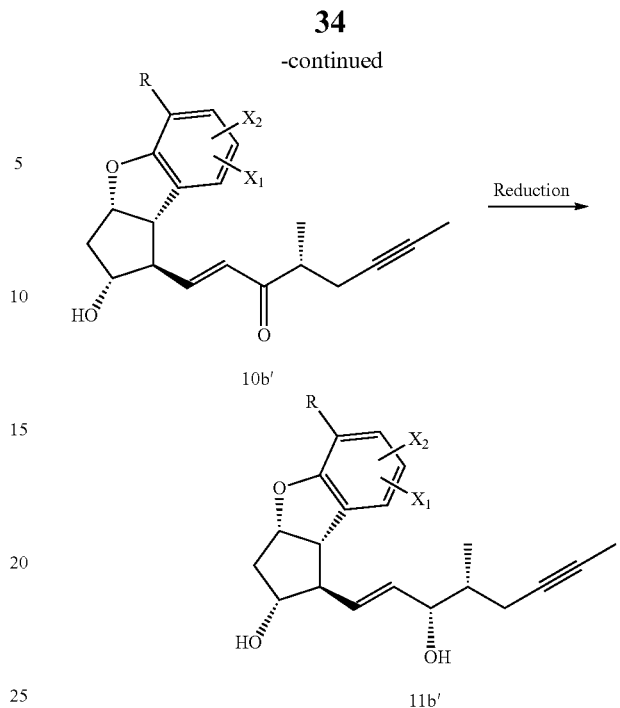

10b'

Reduction →

11b'

An exemplary synthesis scheme for haloalkyne 19' is provided in Scheme 5. For example, compound 19' can be prepared from alcohol D, with by bromination with triphenylphosphine and bromine. Alcohol D can be prepared by the reaction of the chiral oxide 1,2-propylene oxide and propynllithium. In addition to bromoalkynes, other alkylating agents can be used in the alkylation reaction with compound 14', such as other haloalkynes and alkynes with good leaving groups, e.g., sulfonate esters, such as, but not limited to triflates, mesylates, and tosylates. Scheme 5 shows the formation of triflate 20' from alcohol D. The formation of the triflate can be performed, for example, using trifluoromethanesulfonic anhydride in a halogenated solvent in the presence of pyridine. In some embodiments, the presently disclosed subject matter provides an alkylating agent prepared accordingly to Scheme 5 or an analogous haloalkyne or sulfonate ester.

Scheme 5. Synthesis of Alkylating Reagents.

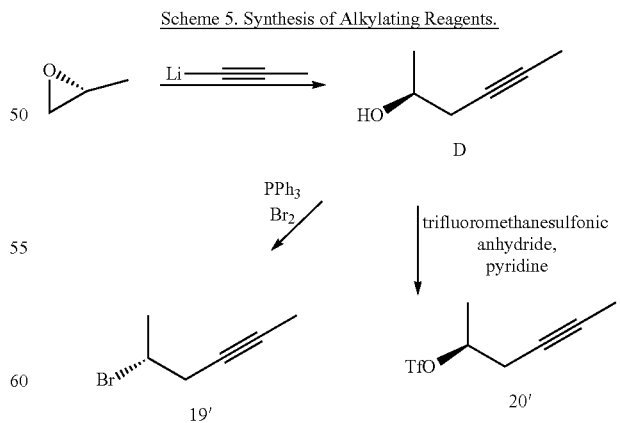

In some embodiments, the presently disclosed subject matter provides a method for preparing a synthetic prostacyclin or synthetic intermediate thereof, wherein the method comprises: (a) providing a compound of formula (V), (V') or (V"):

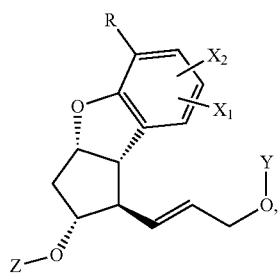
(V)

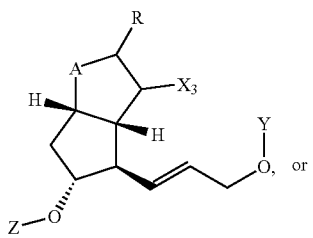
(V')

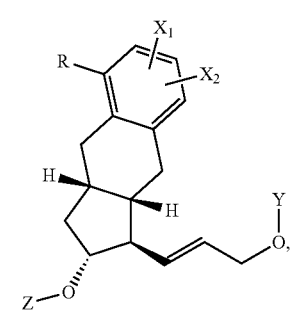
(V")

wherein: R is a directly attached carboxylic acid or ester group or is a carboxylic acid or ester group attached via an aliphatic linker, optionally wherein the aliphatic linker is branched or substituted; $X_1$ and $X_2$ are independently H or an aryl group substituent; $X_3$ is H or an alkyl group substituent; A is —O—, —S—, or —CH$_2$—; and Y and Z are hydroxyl protecting groups, which can be the same or different or a stereoisomer thereof; (b) deprotecting the compound of formula (v), (V') or (V") to provide a diol comprising a primary alcohol and a secondary alcohol; and (c) selectively oxidizing the primary alcohol of the diol to provide an aldehyde-containing compound of one of formulas (XIII), (XIII') or (XIII"):

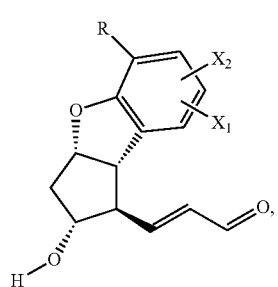
(XIII)

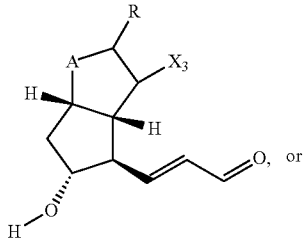
(XIII')

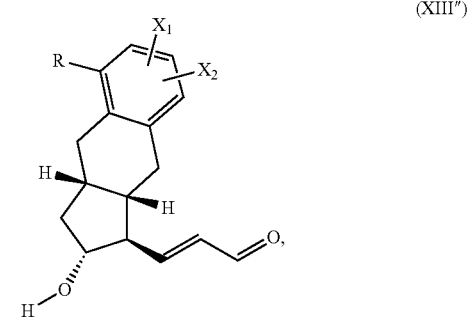
(XIII")

or a stereoisomer thereof, wherein R, $X_1$, $X_2$, $X_3$, and A are as defined for the compounds of formulas (V), (V'), and (V").

In some embodiments, the method comprises or further comprises: (d) protecting the aldehyde-containing compound to provide a protected compound; (e) alkylating the protected compound with a chiral alkyne-containing compound to provide an alkylated compound; and (f) deprotecting the alkylated compound to provide a ketone-containing compound. In some embodiments, the ketone-containing compound has a structure of one of formulas (Xb), (Xb'), and (Xb"):

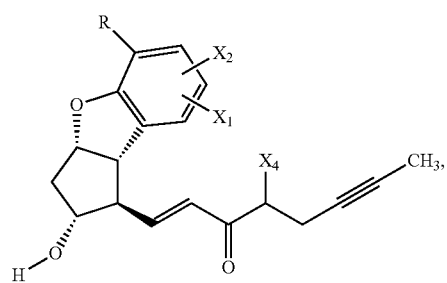
(Xb)

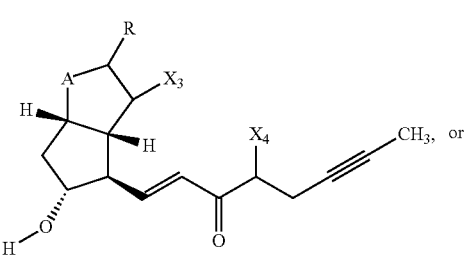
(Xb')

-continued

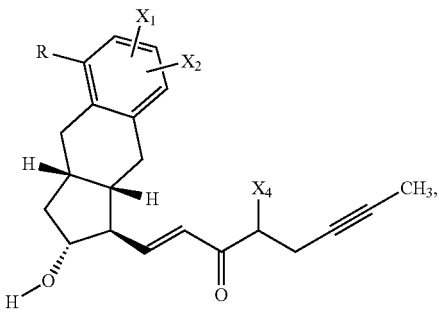

(Xb″)

wherein: R is a directly attached carboxylic acid or ester group or is a carboxylic acid or ester group attached via an aliphatic linker, optionally wherein the aliphatic linker is branched or substituted; $X_1$ and $X_2$ are independently H or an aryl group substituent; $X_3$ is H or an alkyl group substituent; A is —O—, —S—, or —CH$_2$—; and $X_4$ is H, $$\overset{X_5,}{\vdots} \quad \text{or} \quad \overset{X_5,}{\big\downarrow}$$

wherein $X_5$ is alkyl; or a stereoisomer thereof.

In some embodiments, the method comprises or further comprises stereoselectively reducing the ketone of the ketone-containing compound to provide a synthetic prostacyclin. In some embodiments, the stereoselective reduction is performed using a Corey-Bakshi-Shibata (CBS) catalyst. In some embodiments, the synthetic prostacyclin is Beraprost, Iloprost, or Icaprost.

In some embodiments, the method comprises or further comprises reducing alkyne or both alkyne and alkene bonds, to provide, for example Prostacyclin, Carbaprostacyclin, or Treprostinil.

The presently disclosed synthetic routes are both highly versatile and scalable and use readily available or easily prepared starting materials. Each of the individual steps in the synthesis can be performed in good yield. For example, individual steps described herein can typically be performed in 50, 55, 60, 65, 70, 75, 80, or 85% or greater yield, leading to good overall yields of the synthetic prostacyclin or synthetic intermediate thereof.

In some embodiments, the presently described compounds can be prepared as pharmaceutically acceptable salts and/or as solvates, for example, by reaction of a carboxylic acid-containing synthetic prostacyclin with an appropriate base. For instance, the carboxylic acid-containing synthetic prostacyclin can form a sodium salt in a aqueous solution of sodium bicarbonate. Pharmaceutically acceptable salts are described, for example, in Berge et al., (*J. Pharm. Sci.*, 66(1), 1-19 (1977)). The term "pharmaceutically acceptable" can refer to salts (or carriers) that are pharmaceutically acceptable in humans.

Thus, in some embodiments, the presently disclosed compound, their salt and/or solvates, can be admixed with a pharmaceutically acceptable carrier, e.g., to provide a pharmaceutical formulation or composition. In some embodiments, the pharmaceutical formulation of composition is for oral administration.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

Preparation of Aryl Bromide 1

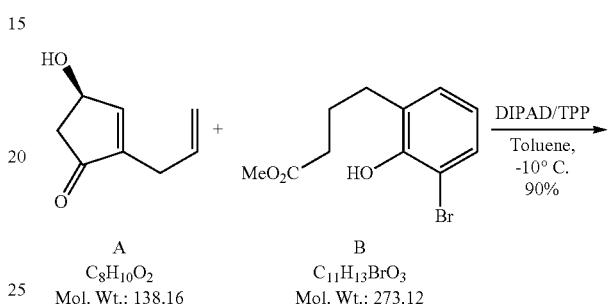

A
$C_8H_{10}O_2$
Mol. Wt.: 138.16

B
$C_{11}H_{13}BrO_3$
Mol. Wt.: 273.12

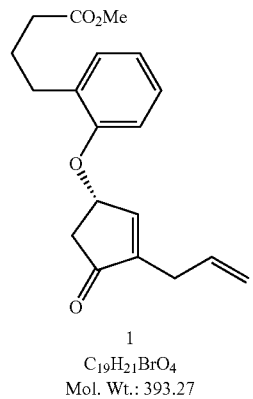

1
$C_{19}H_{21}BrO_4$
Mol. Wt.: 393.27

A 5 liter (L) 3-necked round bottom flask (RBF) equipped with a mechanical stirrer, a temperature probe, a 1 L addition funnel, was charged at room temperature and under nitrogen with 300 g (2.18 mol) A, 654 g (2.39 mol) B, 3.0 liters of anhydrous toluene, and 715 g (2.73 mol) of triphenylphosphine (TPP). The stirring solution was cooled to −10° C. following by a slow addition of 530 g (2.62 mol) of diisopropyldiazodicarboxylate (DIPAD) over 2 hours (hrs or h), so the reaction temperature was maintained below −5° C. The mixture was allowed to stir for 2 additional hrs at ca. −10° C. Thin layer chromatography (TLC) analysis (Hexanes/EtOAc 7:3) indicated complete reaction. The crystallized triphenylphosphine oxide was removed by filtration and washed with 1.5 L of toluene. The combined filtrates were washed with 900 mL of 5% NaHCO$_3$, 600 ml of brine, dried over Na$_2$SO$_4$, filtered and concentrated to dryness to afford ca. 1100 g of viscous brown oil. The crude aryl bromide was purified by silica-gel column chromatography to afford 597 g (70% yield) of 1.

Example 2

Preparation of Ketoester 2

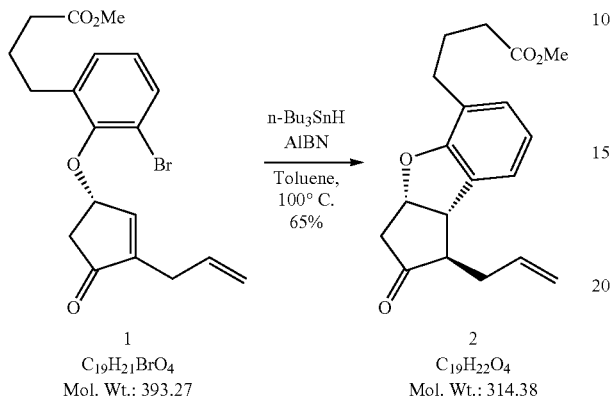

1
C₁₉H₂₁BrO₄
Mol. Wt.: 393.27

2
C₁₉H₂₂O₄
Mol. Wt.: 314.38

A 12 L 3-necked RBF equipped with a magnetic stirrer, a temperature probe, and a 2 L addition funnel, was charged at room temperature, under nitrogen, with 200 g (0.51 mol) of 1 and 5.0 liters of toluene. The stirring solution was degassed three times by introducing nitrogen each time before it was heated to 100° C. To this stirring solution slowly was added at 100° C., via the addition funnel, a solution made up with 205 g (0.76 mol) of tributyltinhydride and 1.8 g (11 mmol) of azobisisobutyronitrile (AIBN) in 1 L of toluene over 3.5 hrs. The mixture was stirred at 100° C. for additional 3 hrs at which time TLC analysis (dichloromethane (DCM)/Hexanes/EtOAc, 5:4.5:0.5) indicated complete reaction. The mixture was concentrated to dryness and purified by silica-gel column chromatography to afford 103 g (64% yield) of the desired 2 as well as 44.1 g (27.5% yield) of its epimer.

Example 3

Preparation of Alcohol 3

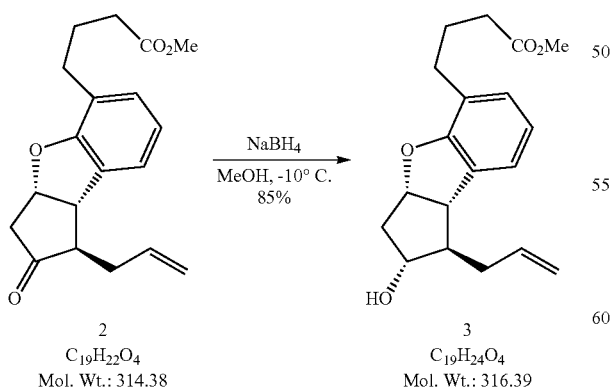

2
C₁₉H₂₂O₄
Mol. Wt.: 314.38

3
C₁₉H₂₄O₄
Mol. Wt.: 316.39

A 3 L 3-necked RBF equipped with a magnetic stirrer, a temperature probe, and an addition funnel, was charged at room temperature, under nitrogen, with 157.2 g (0.5 mol) of 2 and 786 mL of methanol. The reaction solution was cooled to −10° C. and while stirred slowly was added in portions a total of 18.92 g (0.5 mol) of sodium borohydride over 30 minutes (min). During the addition the temperature was maintained below −5° C. The mixture was allowed to stir at −10° C. for another hour and TLC analysis (Hexanes/EtOAC, 7:3) indicated complete reaction. The mixture was quenched at −10° C. with 157.2 mL of 3N hydrochloric acid over 10 min and allowed to stir at room temperature for 10 additional min. The reaction mixture was concentrated by rotary evaporation and extracted with 2×755 mL (1570 mL total) of methyl tert-butyl ether (MTBE). The combined extracts were successively washed with 414.4 mL of 5% sodium bicarbonate, 314.4 mL of brine, dried over sodium sulfate, filtered, concentrated to dryness, and purified by column chromatography to afford 134.5 g (85% yield) of 3.

Example 4

Preparation of 4

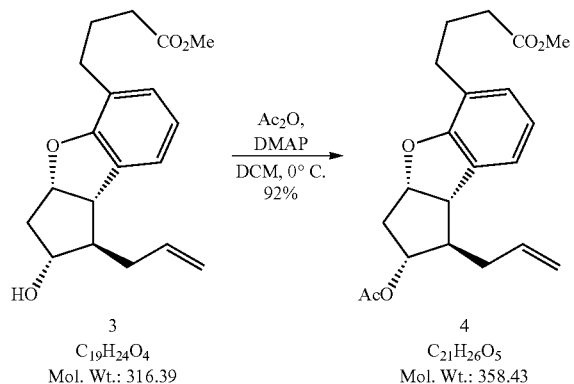

3
C₁₉H₂₄O₄
Mol. Wt.: 316.39

4
C₂₁H₂₆O₅
Mol. Wt.: 358.43

A 1 L 3-necked RBF equipped with a magnetic stirrer, a temperature probe, and an addition funnel, was charged at room temperature, under nitrogen, with 62.88 g (0.2 mol) of 3, 252 mL of dichloromethane, and 25.6 g (0.24 mol) of acetic anhydride (Ac₂O). To the stirring solution was then added dropwise at 0° C. a premixed solution of 29.32 g (0.24 mol) of 4-(dimethylamino)-pyridine (DMAP) and 252 mL of dichloromethane over 30 min. The solution was stirred at 0° C. for 30 min and TLC analysis (Hexanes/EtOAc, 7:3) indicated complete reaction. The reaction mixture was further diluted with 252 mL of dichloromethane and successively was washed with 300 mL of 1N hydrochloric acid, 126 mL of 5% sodium bicarbonate, 189 mL of brine, dried over sodium sulfate, filtered and concentrated to dryness. The crude product was purified by column chromatography to afford 66 g (92% yield) of 4.

Example 5

Preparation of the Allylacetate 5

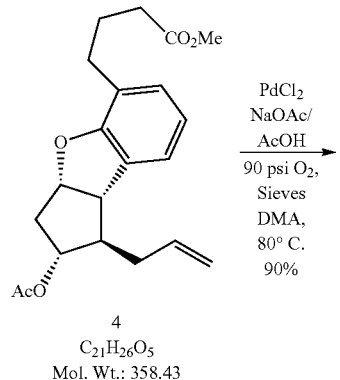

4
$C_{21}H_{26}O_5$
Mol. Wt.: 358.43

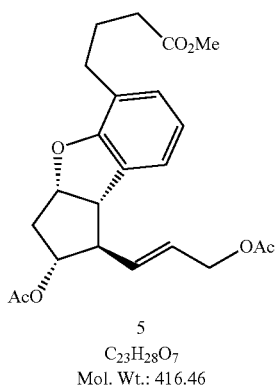

5
$C_{23}H_{28}O_7$
Mol. Wt.: 416.46

A 2 L high-pressure stainless steel reactor was charged at room temperature, with 61.3 g (171 mmol) of 4, 500 mL of dimethylacetamide, 90 mL of acetic acid, 37 g of activated molecular sieves, 2.81 (34.2 mmol) sodium acetate, and 0.3 g (1.8 mmol) of palladium chloride. The reactor was pressurized to 60 psi with oxygen and heated to 80° C. As soon as the temperature stabilized at 80° C., the oxygen pressure was further increase to 90 psi and the mixture was stirred for 30 hrs. TLC analysis (Hexanes/EtOAc, 1:1) indicated complete reaction. The solvent was removed by rotary evaporation and the residue was dissolved in 490 mL of MTBE. The solids were removed by filtration through Celite followed by additional rinse with 123 mL of MTBE. The combined filtrates were concentrated to dryness and the crude product was purified by column chromatography to afford 64.1 g (90% yield) of 5.

Example 6

Preparation of the Alcohol 6

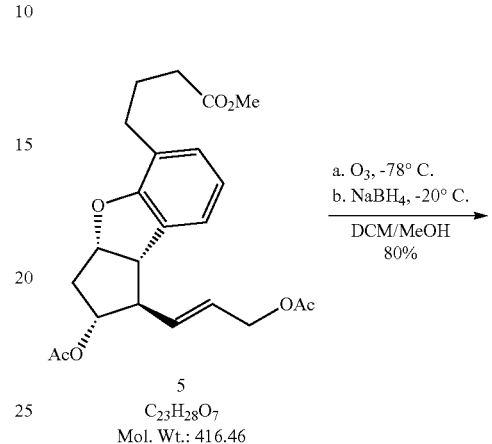

5
$C_{23}H_{28}O_7$
Mol. Wt.: 416.46

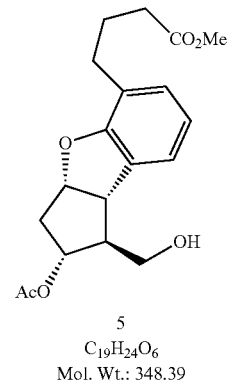

5
$C_{19}H_{24}O_6$
Mol. Wt.: 348.39

A 3 L 3-necked RBF equipped with a magnetic stirrer, a gas inlet, temperature probe, and a dry-ice acetone bath, charged with 62.5 g (150 mmol) of 5, 1.25 L of dichloromethane, and 250 mL of methanol was cooled to −78° C. The stirring solution was purged with ozone, generated by PCI-WEDECO Model GLS-1 Ozonizer at 10 psi pressure with 3 ft³/h oxygen flow and 4% ozone ($O_3$) in Oxygen, over 62.5 min. During ozonolysis the temperature was maintained below −70° C. TLC analysis (Hexanes/EtOAc, 1:1) (a reaction sample was quenched with $Ph_3P$) indicated complete reaction. The mixture was purged with nitrogen gas for 1 hr while it was allowed to warm to −20° C. To the stirring solution, under nitrogen, slowly was added 12.5 g (330 mmol) of sodium borohydride in portions over 30 min, in such a way that foaming (hydrogen evolution) was under control. The reaction mixture was stirred for 30 min while it was allowed to further warm to 0° C. and TLC analysis (Hexanes/EtOAc, 1:1) indicated complete reaction. Following by a slow addition of 330 mL of 4N hydrochloric acid, the reaction mixture was further diluted with 625 mL of water, and the layers were separated. The aqueous layer was back-extracted with 625 mL of dichloromethane. The combined organic extracts were successively washed with 625 mL of brine/water, dried over sodium sulfate, filtered, concentrated, and purified by silica-gel column chromatography to afford 42.3 g (81% yield) of 6.

Example 7

Preparation of the Diol 7

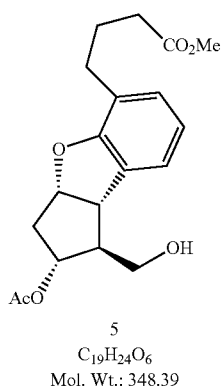

5
C₁₉H₂₄O₆
Mol. Wt.: 348.39 conc. H₂SO₄
MeOH, r.t.
75%

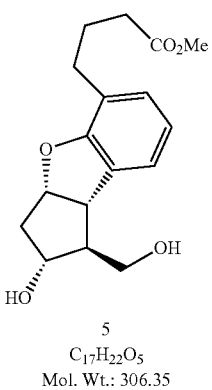

5
C₁₇H₂₂O₅
Mol. Wt.: 306.35

A 500 mL RBF equipped with a magnetic stirrer, was charged at room temperature, under nitrogen, with 45.3 g (130 mmol) of 6 and 136 mL of methanol was cooled to 0° C. To this stirring solution slowly was added via a pipette 0.7 mL (13 mmol) of concentrated sulfuric acid (98%) over 5 min. The mixture was allowed to stir at room temperature for 24 hrs. TLC analysis (Hexanes/EtOAC, 3:7) indicated complete reaction. Followed by the addition of 25 ml 5% NHCO₃, the mixture was concentrated to dryness. To the residue was then added 91 mL of water and 91 mL of MTBE. The mixture was allowed to stir at room temperature for 12 hrs. The formed white suspension was collected by filtration and dried under vacuum. The white solid was further re-crystallized from MTBE to afford 37.5 g (94% yield) of the diol 7.

Example 8

Preparation of the Aldehyde 9

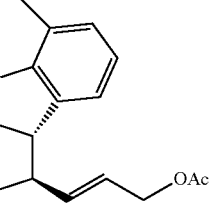

5
C₂₃H₂₈O₇
Mol. Wt.: 416.46 a. O₃, -78° C.
b. Ph₃P, -20° C.
DCM/MeOH
85%

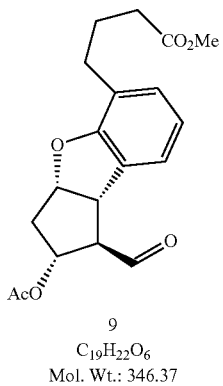

9
C₁₉H₂₂O₆
Mol. Wt.: 346.37

A 2 L 3-necked RBF equipped with a magnetic stirrer, a gas inlet, temperature probe, and a dry-ice acetone bath, charged with 41.7 g (100 mmol) of 5, 800 mL of dichloromethane, and 200 mL of methanol was cooled to -78° C. The stirring solution was purged with ozone, generated by PCI-WEDECO™, Model GLS-1 Ozonizer, at 10 psi pressure with 3 ft³/h oxygen flow and 4% ozone (O₃) in oxygen, over 40 min. During ozonolysis the temperature was maintained below -70° C. TLC analysis (Hexanes/EtOAc, 1:1) (a reaction sample was quenched with Ph₃P) indicated complete reaction. The mixture was purged with nitrogen gas for 1 hr while it was allowed to warm to -20° C. To the stirring solution, under nitrogen, slowly was added 12.5 g (220 mmol) of triphenylphosphine in portions over 30 min. The reaction mixture was stirred for 30 min while it was allowed to further warm to 0° C. and TLC analysis (Hexanes/EtOAc, 1:1) indicated complete reaction. The mixture was diluted with 400 mL of water and continued to stir for 30 min, followed by layer separation. The aqueous layer was back-extracted with 400 mL of dichloromethane. The combined organic extracts were concentrated to dryness. The residue was diluted in 500 mL of MTBE/hexanes (1:4) and washed twice with 250 mL of water/methanol (1:2), and the layers were separated. The aqueous layer was checked for the absence of product. The organic layer was successively washed with 500 mL of brine/water, dried over sodium sulfate, filtered, concentrated to dryness. The residue was further dried under vacuum to afford 35 g (100% yield) of 9. The crude product was forwarded to the next Emmons-Horner coupling.

Example 9

Preparation of Hydroxyl Protected 10

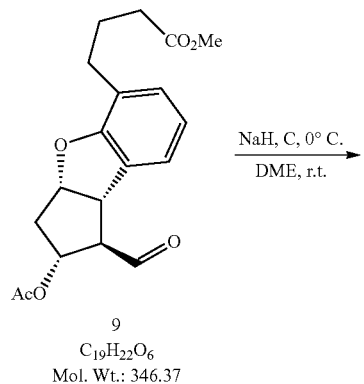

A 1 L 3-necked RBF equipped with a magnetic stirrer, a $N_2$ inlet, temperature probe, and an ice water bath, charged with 200 mL of dimethylether (DME) 25.6 g (110 mmol) of C dissolved in 200 mL of DME. The stirring solution was cooled to 0° C. followed by a slow addition of 2.65 g (110 mmol) of sodium hydride, 55% dispersion in paraffin oil. The mixture was stirred at 0° C. till no more hydrogen gas was generated. To the stirring deprotonated phosphonate, a solution of 35 g (100 mmol) of crude 9 in 200 mL of DME was added at 0° C. over 30 min. The reaction mixture was then allowed to warm to room temperature and stirring continued for another hour. TLC analysis (Hexanes/EtOAc, 1:1) indicated complete reaction. The mixture was diluted with 500 ml of MTBE/hexanes (1:4) and 400 mL of water. The layers were separated and the aqueous layer was back-extracted with 200 mL of MTBE/hexanes (1:4). The combined organic layers were successively washed with 500 ml of brine/water, dried over sodium sulfate, filtered, concentrated, and purified by chromatography to afford 35.3 g (78% yield) of hydroxyl protected 10.

Example 10

Preparation of the Alcohol 11

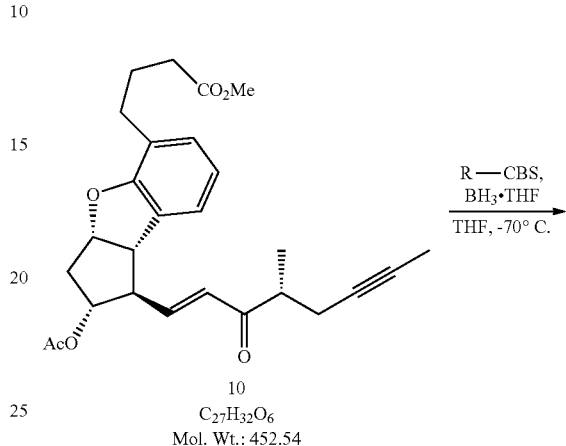

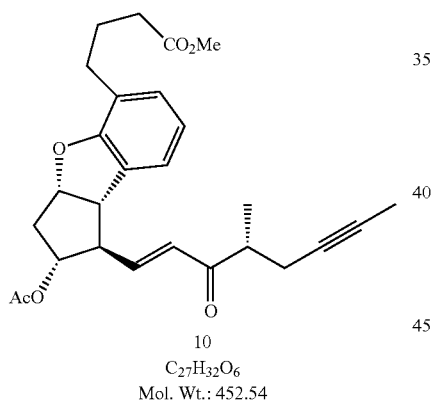

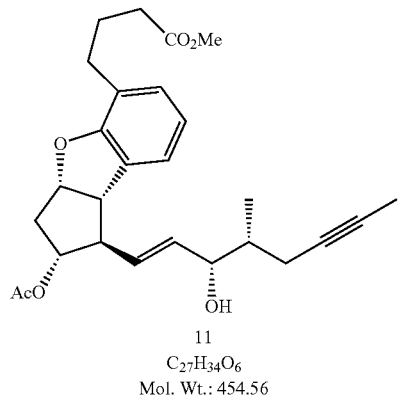

A 500 mL 3-necked RBF equipped with a magnetic stirrer, a $N_2$ inlet, temperature probe, and an dry-ice acetone bath, charged with 100 mL of tetrahydrofuran (THF), 22.73 g (50 mmol) of hydroxyl protected 10, and 5 mL of (R)-(+)-2-methyl-CBS-oxazaborolidine, 1M in THF. The solution was cooled to −78° C., followed by the addition of 50 mL of $BH_3$·THF complex 1M in THF over 1 h maintaining the temperature below −70° C. TLC analysis (Hexanes/EtOAc, 1:1) indicated complete reaction. To the stirring solution slowly was added 50 mL of methanol and allowed to warm to 0° C. over 1 hr. At this temperature the reaction was further quenched with 150 mL of 1N hydrochloric acid. The reaction mixture was diluted with 150 mL of MTBE and the organic layer was separated. The aqueous was back-extracted with 150 mL of MTBE and the combined layers were, successively, washed with 150 mL of water, 150 mL of brine, dried over sodium sulfate, filtered, concentrated, and purified by chromatography to afford 21.7 g (95.3% yield) of diester Beraprost 11, as a single isomer.

Example 11

Preparation of Beraprost Acid Single Isomer

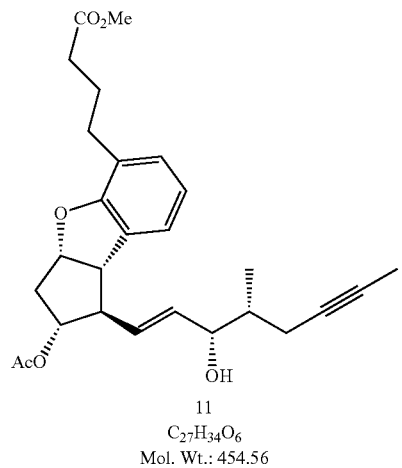

11
C27H34O6
Mol. Wt.: 454.56

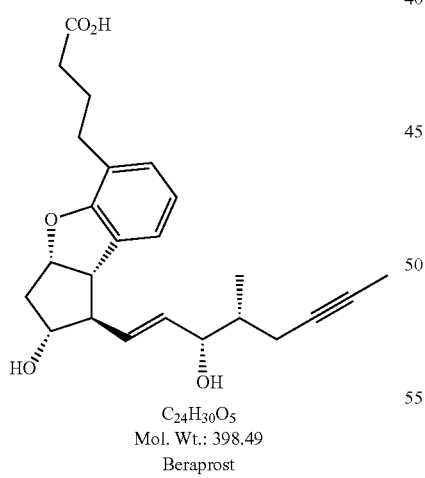

C24H30O5
Mol. Wt.: 398.49
Beraprost 50 mL 3N RBF was charged with 580 mg (1.27 mmol) 11 in 5 mL MeOH. 356 mg (8.9 mmol) NaOH dissolved in 2 mL water was added. The mixture was stirred at 20° C. for 3 h. The mixture was cooled to 0° C. and 1M HCl was added to get pH=3. The product was extracted with 50 mL MTBE, washed with 2×10 mL brine and dried over sodium sulfate. The solution was concentrated in vacuum to afford crude Beraprost acid. The material was purified on silica gel column eluting with hexane:AcOEt 1:1 (V/V) to afford 300 mg pure Beraprost acid (59%).

Example 12

Preparation of Compound 13

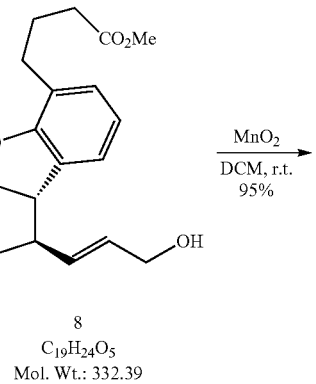

8
C19H24O5
Mol. Wt.: 332.39

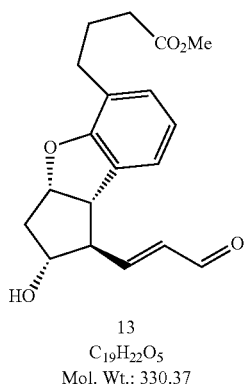

13
C19H22O5
Mol. Wt.: 330.37

A 500 mL 3-necked RBF equipped with a mechanical stirrer, a temperature probe was charged at room temperature and under nitrogen with 10 g (30.1 mmol) 8, 13 g (150 mmol) MnO2 and 100 mL of dichloromethane. The solution was stirred at 20° C. for 20 hrs, TLC analysis (Hexanes/EtOAc 7:3) indicated complete reaction. The mixture was filtered and concentrated to dryness to afford ca. 9.4 g of (95% yield) of 13.

Example 13

Preparation of Compound 14

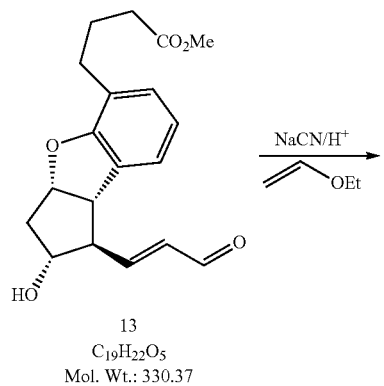

13
C$_{19}$H$_{22}$O$_5$
Mol. Wt.: 330.37

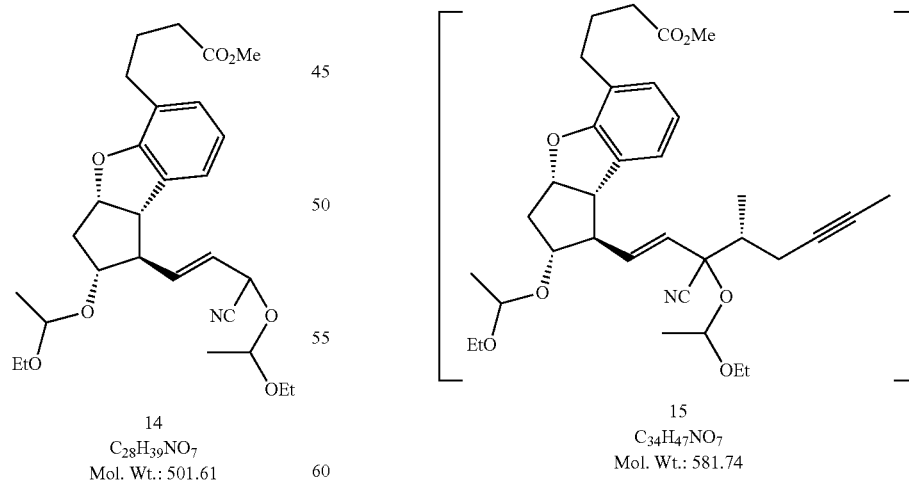

14
C$_{28}$H$_{39}$NO$_7$
Mol. Wt.: 501.61

A 500 mL 3-necked RBF equipped with a mechanical stirrer, a temperature probe, was charged at room temperature and under nitrogen with 9 g (27.2 mmol) 13, 100 mL of anhydrous THF, 4.3 g (60 mmol) ethyl vinyl ether, 3.4 g (30 mmol) and 1.5 g sodium cyanide. The solution was stirred at 20° C. for 20 hrs, TLC analysis (Hexanes/EtOAc 7:3) indicated complete reaction. The mixture containing 14 was processed to next step.

Example 14

Preparation of Compound 15

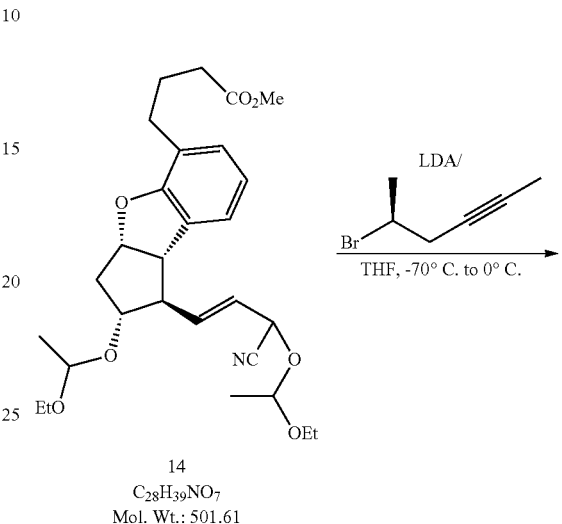

15
C$_{34}$H$_{47}$NO$_7$
Mol. Wt.: 581.74

The mixture containing 14 (27 mmol) was cooled to −70° C. and was charged 15 mL (30 mmol) of lithium diisopropylamide (LDA; 2.0 M in THF) and 5.2 g (32 mmol) 5-bromo-hex-2-yne slowly keeping temperature at −70° C. The mixture was warmed to 0° C. over 3 hrs. TLC analysis (Hexanes/

EtOAc 7:3) indicated complete reaction. The mixture containing 15 was processed to next step.

Example 15

Preparation of Hydroxyl Deprotected 10

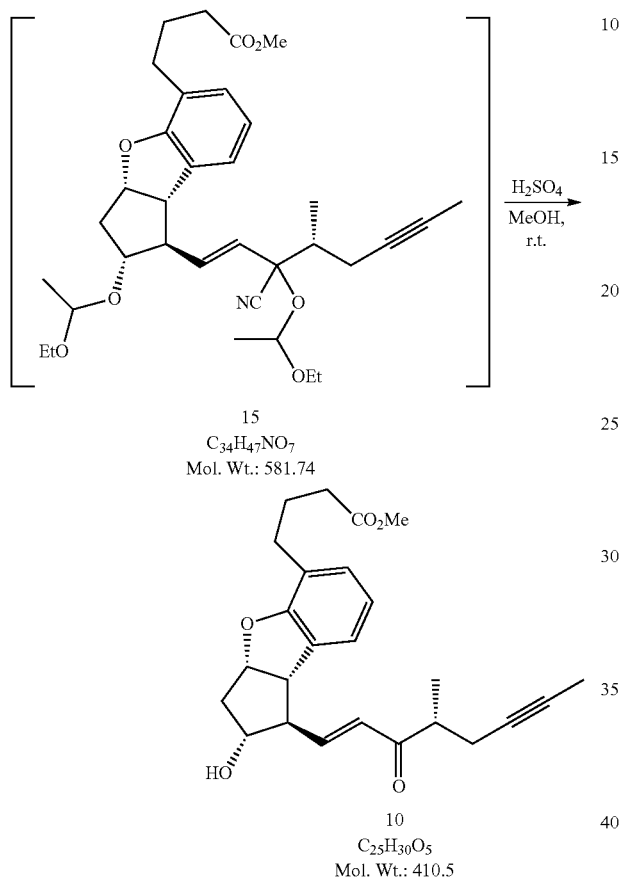

15
C$_{34}$H$_{47}$NO$_7$
Mol. Wt.: 581.74

10
C$_{25}$H$_{30}$O$_5$
Mol. Wt.: 410.5

The mixture containing 15 (27 mmol) was maintained at 0° C. and was charged 40 mL of 5% H$_2$SO$_4$ containing methanol and warmed 20° C. The mixture was stirred for 12 hrs. TLC analysis (Hexanes/EtOAc 1:1) indicated complete reaction. The mixture was concentrated to half volume and diluted with 50 ml of MTBE/Hexanes (1:4) and 40 mL of water. The layers were separated and the aqueous layer was back-extracted with 20 mL of MTBE/Hexanes (1:4). The combined organic layers were successively washed with 50 mL of Brine/Water, dried over sodium sulfate, filtered, concentrated, and purified by chromatography to afford 4.4 g (40% yield) of hydroxyl deprotected 10.

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A method for preparing a synthetic prostacyclin or a synthetic intermediate thereof, wherein the method comprises contacting an aldehyde with an enantiomerically pure phosphonate in a Horner-Emmons reaction to provide an alkene, wherein the enantiomerically pure phosphonate has a structure:

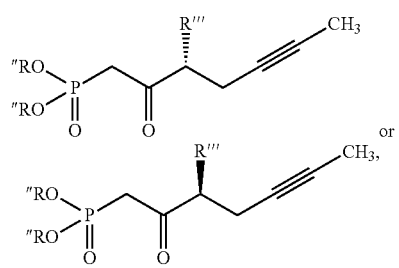

wherein R″ and R″' are alkyl; and
wherein the synthetic prostacyclin or synthetic intermediate thereof is produced as a single isomer.

2. The method of claim 1, wherein the aldehyde is a product of the ozonolysis of a compound of formula (V), (V') or (V″):

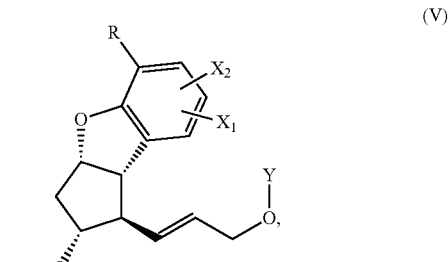

(V)

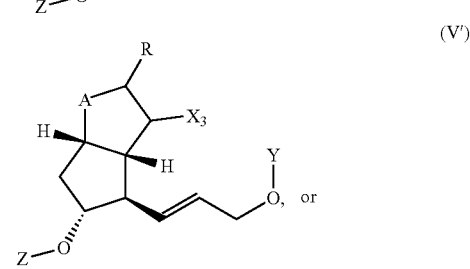

(V')

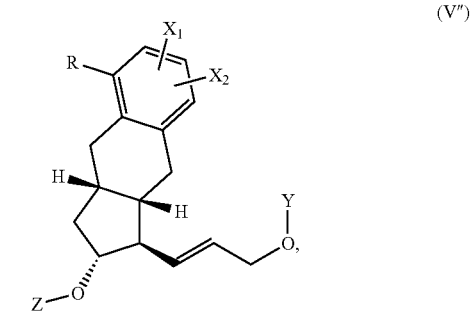

(V″)

wherein:
R is a directly attached carboxylic acid or ester group or is a carboxylic acid or ester group attached via an aliphatic linker, optionally wherein the aliphatic linker is branched or substituted;
X$_1$ and X$_2$ are independently H or an aryl group substituent;
X$_3$ is H or an alkyl group substituent;
A is —O—, —S—, or —CH$_2$—; and
Y and Z are hydroxyl protecting groups, which can be the same or different;
or a stereoisomer thereof.

3. The method of claim 2, wherein R is —CO$_2$R', —(CH$_2$)$_n$—CO$_2$R', —O—(CH$_2$)$_n$—CO$_2$R', or —CH$_2$=CH$_2$—(CH$_2$)$_n$—CO$_2$R', wherein n is an integer between 1 and 8 and R' is H, unsubstituted alkyl, substituted alkyl, aryl, or substituted aryl.

4. The method of claim 2, wherein Y and Z are each —C(=O)CH$_3$.

5. The method of claim 2, wherein the aldehyde is the product of the ozonolysis of a compound of formula (V):

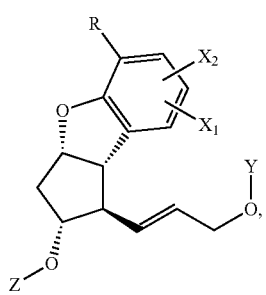

(V)

wherein:
R is a directly attached carboxylic acid or ester group or is a carboxylic acid or ester group attached via an aliphatic linker, optionally wherein the aliphatic linker is branched or substituted;
X$_1$ and X$_2$ are independently H or an aryl group substituent; and
Y and Z are hydroxyl protecting groups, which can be the same or different;
or a stereoisomer thereof.

6. The method of claim 5, wherein the compound of formula (V) is the compound:

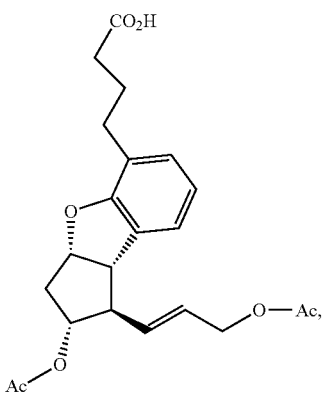 [SMILES: CC(=O)OC/C=C/[C@@H]1[C@H]2c3cccc(CCCC(=O)O)c3O[C@H]2C[C@H]1OC(C)=O]

or a stereoisomer thereof.

7. The method of claim 1, further comprising stereoselectively reducing a ketone in the alkene compound formed during the Horner-Emmons reaction.

8. The method of claim 7, wherein the stereoselective reduction is performed using a Corey-Bakshi-Shibata (CBS) catalyst.

9. The method of claim 1, further comprising deprotecting protected hydroxyl groups.

10. The method of claim 1, wherein the synthetic prostacyclin is Beraprost.

11. A synthetic prostacyclin or synthetic intermediate thereof, prepared according to the method of claim 1.

12. A synthetic prostacyclin prepared according to the method of claim 1, wherein the synthetic prostacyclin is a single isomer of Beraprost.

13. A method for preparing a synthetic prostacyclin or synthetic intermediate thereof, wherein the method comprises:

(a) providing a compound of formula (V), (V') or (V"):

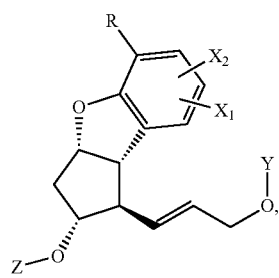

(V)

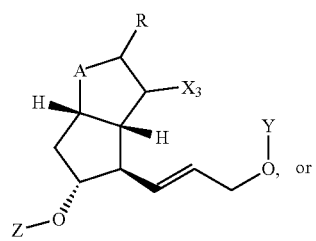

(V')

or

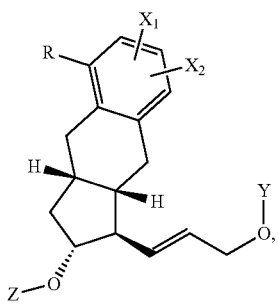

(V")

wherein:
R is a directly attached carboxylic acid or ester group or is a carboxylic acid or ester group attached via an aliphatic linker, optionally wherein the aliphatic linker is branched or substituted;
X$_1$ and X$_2$ are independently H or an aryl group substituent;
X$_3$ is H or an alkyl group substituent;
A is —O—, —S—, or —CH$_2$—; and
Y and Z are hydroxyl protecting groups, which can be the same or different;
or a stereoisomer thereof;

(b) deprotecting the compound of formula (V), (V') or (V") to provide a diol comprising a primary alcohol and a secondary alcohol; and (c) selectively oxidizing the primary alcohol of the diol to provide an aldehyde-containing compound of one of formulas (XIII), (XIII') or (XIII"):

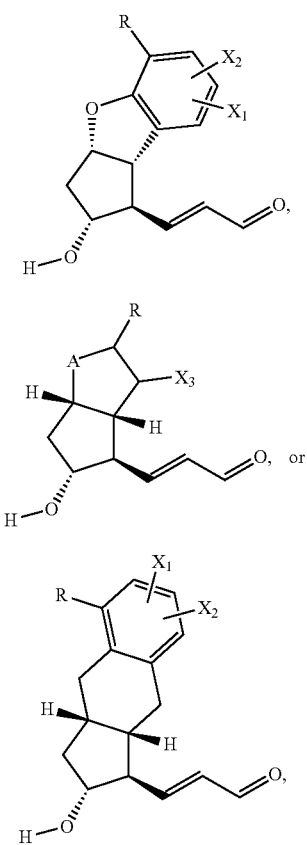

or a stereoisomer thereof, wherein R, $X_1$, $X_2$, $X_3$, and A are as defined for the compounds of formulas (V), (V'), and (V").

14. A method for producing a compound of formula (V), wherein the method comprises:
(a) coupling compound A:

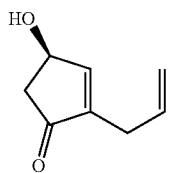

or a stereoisomer thereof, and
a compound of formula (B):

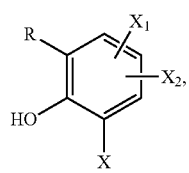

wherein:
X is halo,
R is a directly attached carboxylic acid or ester group or is a carboxylic acid or ester group attached via an aliphatic linker, optionally wherein the aliphatic linker is branched or substituted; and
$X_1$ and $X_2$ are independently H or an aryl group substituent;
(b) cyclizing the product of step (a) to form a cyclized compound;
(c) reducing a ketone group in the cyclized compound to form a compound comprising a secondary alcohol; and
(d) performing an oxidative rearrangement of the compound prepared in step (c) or a compound prepared by protecting the secondary alcohol group of the compound prepared in step (c).

15. A method for preparing a synthetic prostacyclin or synthetic intermediate thereof, wherein the method comprises the use of a synthetic intermediate of formula (V), (V'), or (V") or a hydroxyl group deprotected derivative thereof, wherein formulas (V), (V'), and (V") are:

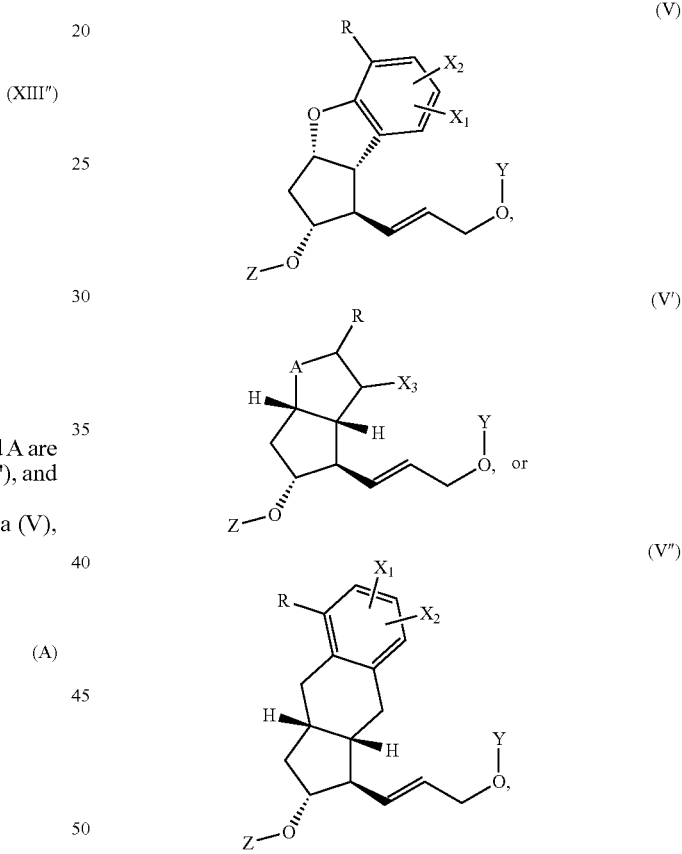

wherein:
R is a directly attached carboxylic acid or ester group or is a carboxylic acid or ester group attached via an aliphatic linker, optionally wherein the aliphatic linker is branched or substituted;
$X_1$ and $X_2$ are independently H or an aryl group substituent;
$X_3$ is H or an alkyl group substituent;
A is —O—, —S—, or —$CH_2$—; and
Y and Z are hydroxyl protecting groups, which can be the same or different; or a stereoisomer thereof, and
wherein the hydroxyl group deprotected derivative thereof is a compound of one of formulas (V), (V'), and (V") wherein one or both of Z and Y are replaced by a hydrogen atom.

16. A compound of formula (V), (V'), or (V'') or a hydroxyl group deprotected derivative thereof, wherein formulas (V), (V'), and (V'') are:

(V)

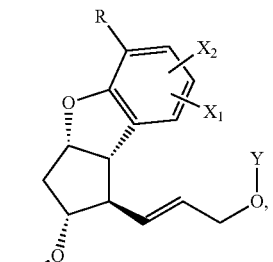

(V')

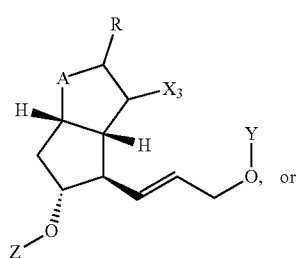

(V'')

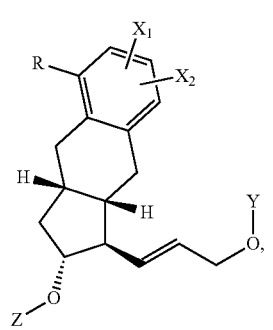

wherein:
R is a directly attached carboxylic acid or ester group or is a carboxylic acid or ester group attached via an aliphatic linker, optionally wherein the aliphatic linker is branched or substituted;
$X_1$ and $X_2$ are independently H or an aryl group substituent;
$X_3$ is H or an alkyl group substituent;
A is —O—, —S—, or —CH$_2$—; and
Y and Z are hydroxyl protecting groups, which can be the same or different; or a stereoisomer thereof, and
wherein the hydroxyl group deprotected derivative thereof is a compound of one of formulas (V), (V'), and (V'') wherein one or both of Z and Y are replaced by a hydrogen atom.

17. A method for preparing an intermediate for a synthetic prostacyclin, wherein the method comprises contacting compound A:

(A)

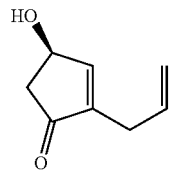

or a stereoisomer and/or analog thereof with a halogenated coupling precursor molecule in a coupling reaction to provide a coupled halogenated molecule.

18. A compound of formula (XIV), (XIV'), or (XIV''):

(XIV)

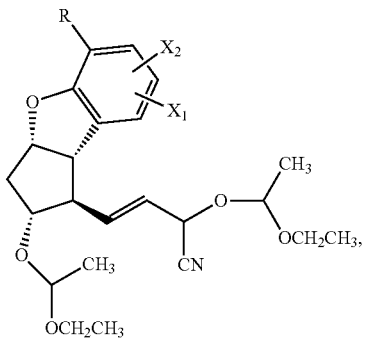

(XIV')

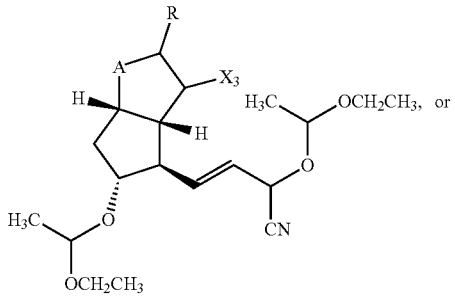

(XIV'')

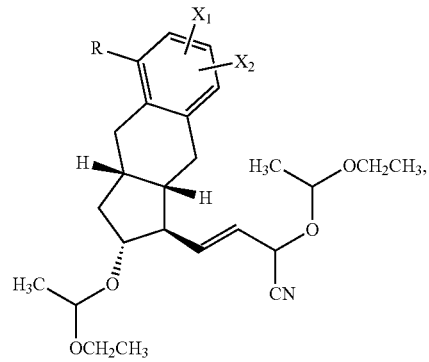

wherein:
R is a directly attached carboxylic acid or ester group or is a carboxylic acid or ester group attached via an aliphatic linker, optionally wherein the aliphatic linker is branched or substituted;
$X_1$ and $X_2$ are independently H or an aryl group substituent;
$X_3$ is H or an alkyl group substituent; and
A is —O—, —S—, or —CH$_2$—;
or a stereoisomer thereof.

19. A method of preparing a synthetic prostacyclin, wherein the method comprises alkylating a compound of formula (XIV), (XIV'), or (XIV").

* * * * *